(12) United States Patent
Anderson

(10) Patent No.: US 12,343,041 B2
(45) Date of Patent: Jul. 1, 2025

(54) CANNULATED T-HANDLE DRIVER AND DOUBLE LATCH CANNULA OBTURATOR

(71) Applicant: Conmed Corporation, Utica, NY (US)

(72) Inventor: Sharon Anderson, St. Petersburg, FL (US)

(73) Assignee: Conmed Corporation, Utica, NY (US)

(*) Notice: Subject to any disclaimer, the term of this patent is extended or adjusted under 35 U.S.C. 154(b) by 630 days.

(21) Appl. No.: 17/277,561

(22) PCT Filed: Sep. 24, 2019

(86) PCT No.: PCT/US2019/052546
§ 371 (c)(1),
(2) Date: Mar. 18, 2021

(87) PCT Pub. No.: WO2020/068715
PCT Pub. Date: Apr. 2, 2020

(65) Prior Publication Data
US 2022/0031359 A1    Feb. 3, 2022

Related U.S. Application Data

(60) Provisional application No. 62/735,246, filed on Sep. 24, 2018.

(51) Int. Cl.
*A61B 17/34* (2006.01)
*A61B 17/00* (2006.01)
*A61B 17/88* (2006.01)

(52) U.S. Cl.
CPC ...... *A61B 17/3496* (2013.01); *A61B 17/3423* (2013.01); *A61B 2017/00424* (2013.01); *A61B 2017/0046* (2013.01); *A61B 17/8875* (2013.01)

(58) Field of Classification Search
CPC ............ A61B 17/3496; A61B 17/3423; A61B 17/8875; A61B 2017/00424;
(Continued)

(56) References Cited

U.S. PATENT DOCUMENTS

| | | | |
|---|---|---|---|
| 4,808,168 A | * | 2/1989 | Warring ............. A61M 13/003 604/170.02 |
| 4,996,896 A | | 3/1991 | Bachand et al. |

(Continued)

FOREIGN PATENT DOCUMENTS

| | | |
|---|---|---|
| CN | 203031521 | 7/2013 |
| CN | 203945305 | 11/2014 |

(Continued)

OTHER PUBLICATIONS

CN Office Action, dated Mar. 23, 2021, for Patent Application No. 2020-511740, pp. 1-4.

(Continued)

*Primary Examiner* — Shaun L David
*Assistant Examiner* — Rachael L Geiger
(74) *Attorney, Agent, or Firm* — Bond, Schoeneck & King, PLLC; Frederick J. M. Price

(57) ABSTRACT

An obturator assembly with a rotatable and cannulated obturator shaft for inserting a cannula into a human joint space. The obturator assemblies includes an elongated body having a proximal end and a distal end with a channel extending along an inner surface of the elongated body. The obturator assembly also includes a locking mechanism connected within the elongated body. The locking mechanism is rotatable between a first configuration and a second configuration. A cannulated obturator shaft is attached to the locking mechanism and is rotatable between the first configuration and the second configuration via the locking mechanism. The obturator assembly has a latch assembly connected to the cannulated obturator shaft which is rotatable between the first configuration and second configuration via the locking mechanism. The latch assembly securely and removably attaches to a cannula.

18 Claims, 28 Drawing Sheets

(58) Field of Classification Search
CPC .... A61B 2017/0046; A61B 2017/0042; A61B 2017/291; A61B 17/3421; A61B 2017/347; B25G 1/06
See application file for complete search history.

(56) References Cited

U.S. PATENT DOCUMENTS

| | | | | |
|---|---|---|---|---|
| 5,104,382 | A * | 4/1992 | Brinkerhoff | A61B 17/3496 604/164.12 |
| 5,290,243 | A * | 3/1994 | Chodorow | A61B 17/3496 604/164.12 |
| 5,464,407 | A | 11/1995 | McGuire | |
| 6,221,029 | B1 * | 4/2001 | Mathis | A61B 10/0233 600/564 |
| 7,226,456 | B2 | 6/2007 | O'Neil et al. | |
| 7,287,450 | B1 * | 10/2007 | Liao | B25B 15/02 81/177.9 |
| 9,216,049 | B2 | 12/2015 | Rabiner et al. | |
| 9,919,412 | B2 | 3/2018 | Petit | |
| 10,194,969 | B2 | 2/2019 | Overes et al. | |
| 10,575,888 | B2 | 3/2020 | Coillard-Lavirotte et al. | |
| 2015/0141914 | A1 * | 5/2015 | Fasano | A61M 25/0113 604/95.01 |
| 2016/0143682 | A1 * | 5/2016 | Overes | A61B 17/8875 606/104 |
| 2019/0029758 | A1 * | 1/2019 | Householder | A61B 17/3403 |

FOREIGN PATENT DOCUMENTS

| | | | |
|---|---|---|---|
| CN | 111212610 A | 5/2020 | |
| DE | 3643784 A1 | 7/1987 | |
| EP | 0451932 A1 | 10/1991 | |
| FR | 2990838 | 11/2013 | |
| WO | WO-2005092202 A1 * | 10/2005 | ......... A61B 17/3417 |
| WO | 2016/130794 | 8/2016 | |
| WO | WO-2019046359 A1 * | 3/2019 | ......... A61B 17/8875 |

OTHER PUBLICATIONS

International Search Report Form PCT/ISA/220, International Application No. PCT/US2019/052546, pp. 1-15, Dated Mar. 9, 2020.
International Search Report Form PCT/ISA/220, International Application No. PCT/US2019/048434, pp. 1-9, Dated Dec. 11, 2018.
JP Office Action, App. No. 2021-516417, dated Jun. 28, 2022, pp. 1-19.
CN Office Action 2, Application No. 201980062853.9, dated Nov. 28, 2024, entire document.

* cited by examiner

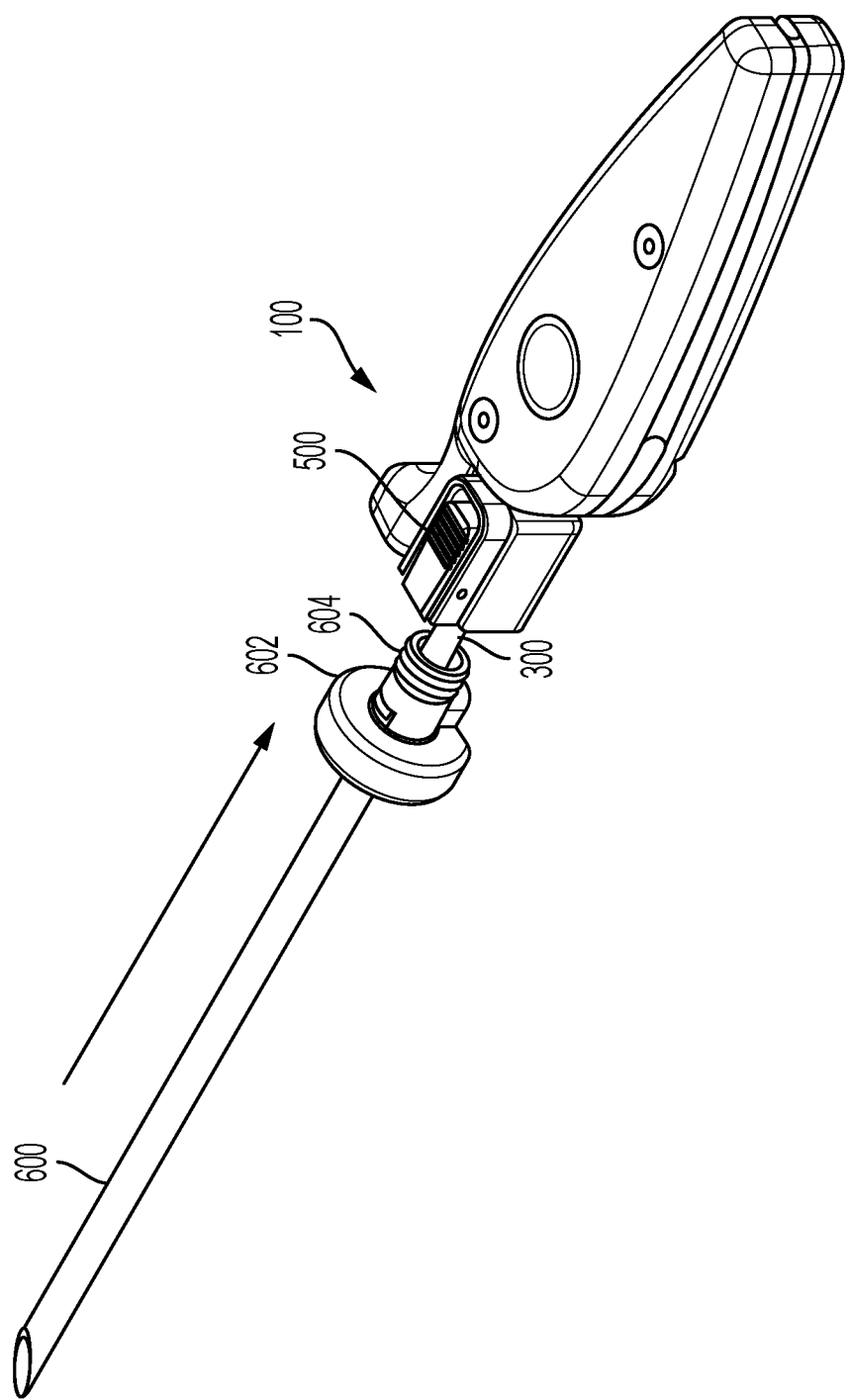

CANNULATED T-HANDLE DRIVER AND DOUBLE LATCH CANNULA OBTURATOR

CROSS-REFERENCES TO RELATED APPLICATIONS

This application is a national stage application under 35 U.S.C. 371 based on international patent application PCT/US19/52546 filed on Sep. 24, 2019, which claims priority to U.S. Provisional Patent Application Ser. No. 62/735,246, filed on Sep. 24, 2018, the entireties of which are incorporated herein by reference.

BACKGROUND OF THE INVENTION

1. Field of the Invention

The invention relates generally to an obturator for inserting a cannula into the human joint space and, more particularly, to an obturator assembly with a rotatable cannulated shaft for inserting a cannula.

2. Description of Related Art

Cannulas are often used in orthopedic surgeries to provide a means of placing instrumentation into the joint space. A manual obturator is frequently used to provide a means of a traumatically inserting a cannula to a specific position or depth into the joint space. In a surgical environment, fluids can make gripping these obturators more difficult. This is especially true when saline, blood, and/or lipids are involved. When the conditions are such that gripping the obturator is more difficult, there is less torque to insert the cannula to the specific position or depth into the joint space. As a result, the surgeon must take additional time and caution to insert the cannula into the joint space to prevent tissue and cartilage damage.

There have been attempts to provide a better grip for the obturator, including altering the size of the handle. As shown in FIG. 26, an example, the handle of a certain conventional obturator is oversized to provide additional surface area for gripping the obturator. However, the oversized handles are fixed to the obturator shaft. Thus, the obturator shaft is at a fixed angle relative to the handle. Therefore, the obturator shaft can be difficult to manipulate for certain surgical sites and locations.

Therefore, there is a need for an obturator for providing additional torque at multiple angles with a variety of desired holding positions.

SUMMARY OF THE INVENTION

The present disclosure is directed to embodiments of an obturator assembly with a rotatable and cannulated obturator shaft, of multiple diameters, for inserting a cannula into the joint space using a variety of hand positions. The obturator assembly can include an elongated body having a proximal end and a distal end with a channel extending along an inner surface within the elongated body. The obturator assembly can also include a locking mechanism connected within the elongated body. The locking mechanism is rotatable between a first configuration and a second configuration. A cannulated obturator shaft is removably attached or fixed to the locking mechanism and is rotatable between the first configuration and the second configuration via the locking mechanism.

According to another aspect, the obturator assembly can include an elongated body having a proximal end and a distal end. A channel extends along an inner surface within the elongated body. The obturator assembly can also include a cannulated hub rotatably connected to the elongated body in the recess. The cannulated hub is rotatable between a first configuration and a second configuration and a locking mechanism integrated therewith. A cannulated obturator shaft is removably attached or fixed to the locking mechanism and is rotatable between the first configuration and the second configuration via the locking mechanism. The obturator assembly also includes a latch assembly connected to the cannulated obturator shaft.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

FIG. 27 is a perspective view schematic representation of an obturator assembly in the first configuration showing a cannula being assembled to the obturator assembly using a latch connection, according to an embodiment.

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
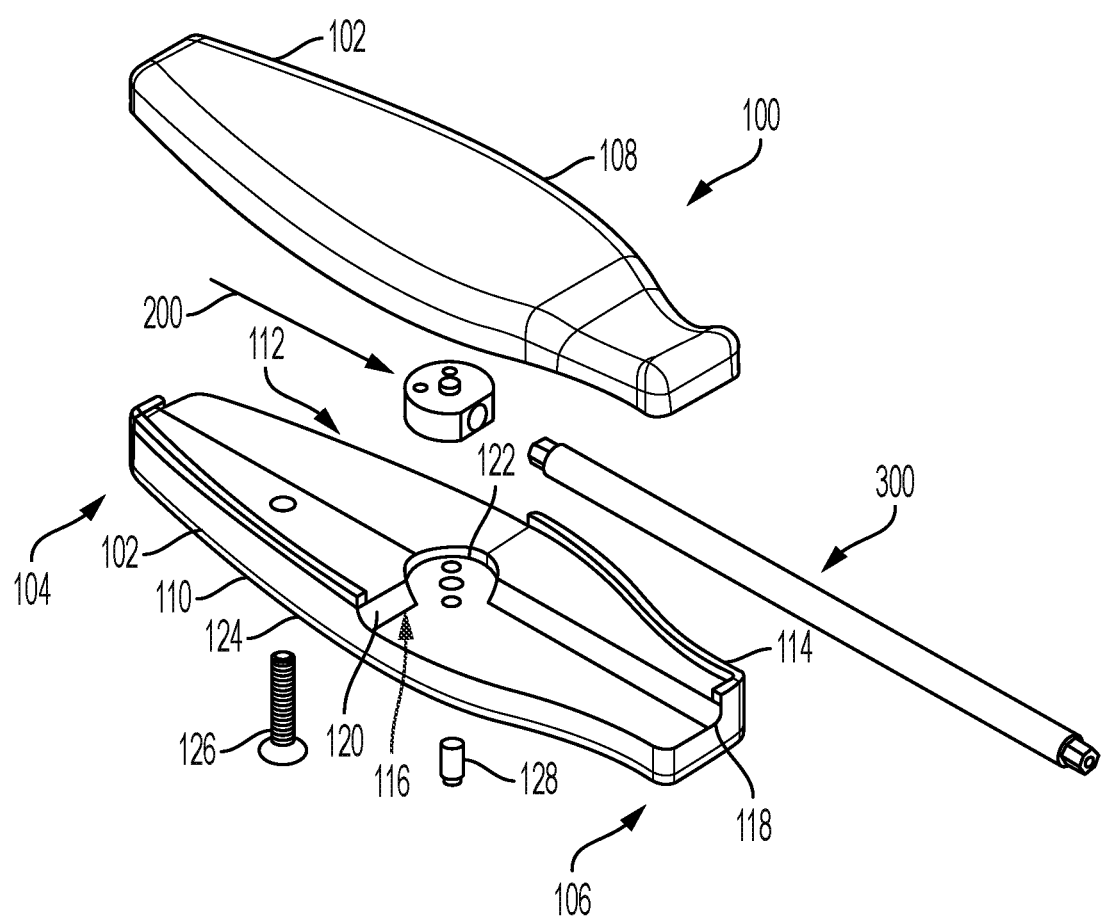
FIG. 1 is an exploded view schematic representation of a driver assembly, according to an embodiment.

Referring now to the figures, wherein like reference numerals refer to like parts throughout, FIG. 1 shows an exploded view schematic representation of a driver assembly 100. In the depicted embodiment, the driver assembly 100 comprises an elongated body 102 extending between a proximal end 104 and a distal end 106. The elongated body 102 and any of other component parts of the driver assembly 100 can be composed of disposable or reusable material. Further, the driver assembly 100 can be manufactured or otherwise assembled to prevent or allow disassembly. The elongated body 102 can be ergonomically designed to improve the grip of the user on the elongated body 102. In the embodiment shown in FIG. 1, the elongated body 102 comprises a first piece 108 and a second piece 110 both sized and configured to align and connect, forming an inner volume 112 of the elongated body 102.

Still referring to FIG. 1, the second piece 110 of the elongated body 102 comprises a first channel 114 and a second channel 116 extending partially therethrough. The first and second channels 114, 116 extend from separate exit points 118, 120 along the elongated body 102 and converge at a central recess 122 in the second piece 110, as shown. In the depicted embodiment, the first channel 114 extends from an exit point 118 at the distal end 106 of the second piece 110 and the second channel 116 extends from an exit point 120 on a first side 124 of the elongated body 102 between the proximal and distal ends 104, 106. In the embodiment shown in FIG. 1, the first channel 114 extends perpendicular to the second channel 116. However, other angular relationships between the first channel 114 and the second channel 116 can be implemented in the elongated body 102 (as should be understood by a person of ordinary skill in the art in conjunction with a review of this disclosure).

As shown in FIG. 1, one or more connectors 126, such as screws or dowel pins, are used to connect the first piece 108 and the second piece 110 of the elongated body 102 as well as other components of the driver assembly 100. A cannulated hub 200 is sized or otherwise configured to fit into the recess 122 within the second piece 110, and is configured to rotate a driver shaft 300 (as used herein, the terms "driver shaft" can be used interchangeably with "obturator shaft" or any other similar tubular structure, depending on the intended use). The cannulated hub 200 is rotatable within the recess 122 via a locking mechanism 128. The locking mechanism 128 can be used to hold the driver shaft 300 in the first configuration and the second configuration with a predetermined force that can be overcome with relatively low force (automatic spring action, or manual user actuation) to allow the driver shaft 300 to rotate about the cannulated hub 200. In the depicted embodiment, the locking mechanism 128 is a spring-loaded detent; however alternative similar connectors may be used.

Figure 2:
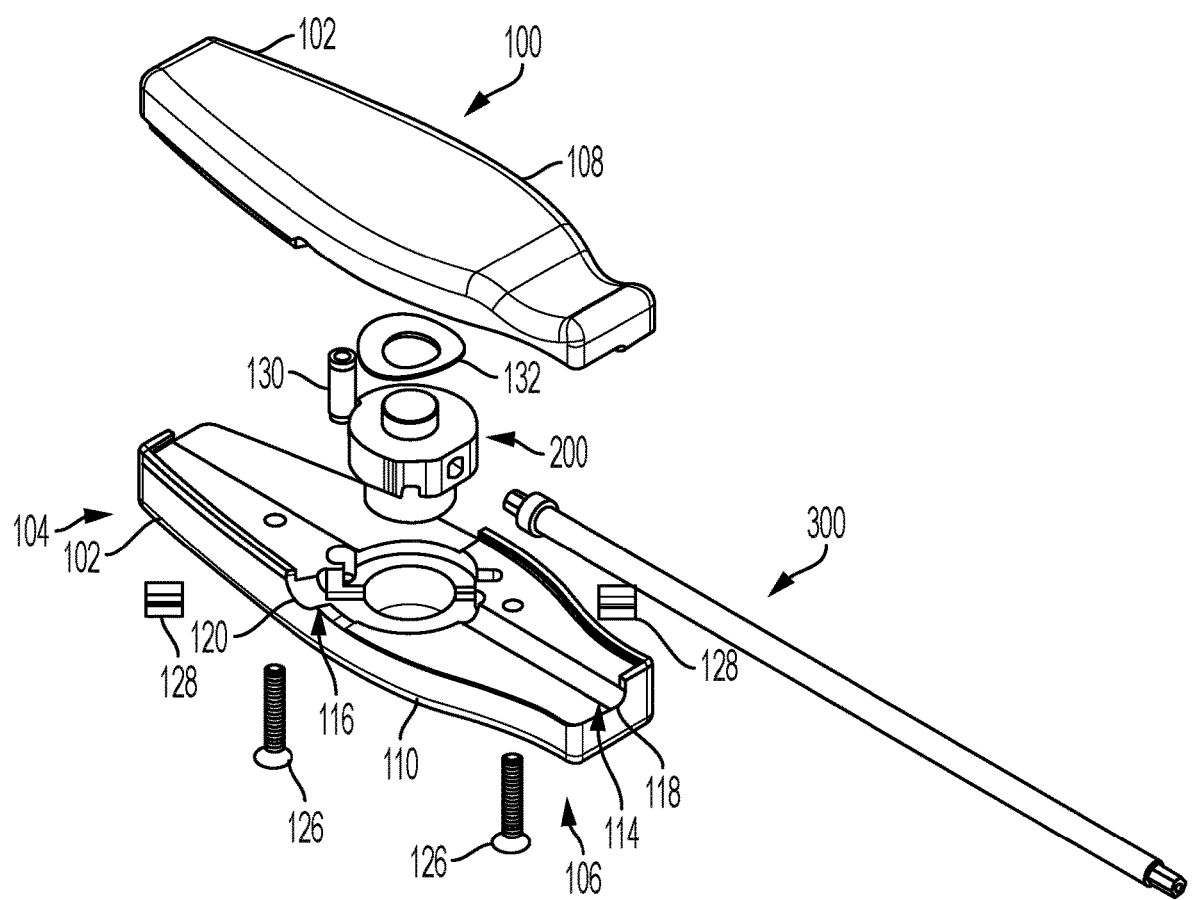
FIG. 2 is an exploded view schematic representation of a driver assembly, according to an alternative embodiment.

An alternative embodiment of the driver assembly 100 is shown in FIG. 2. In the embodiment shown in FIG. 2, the locking mechanism 128 can be one or more keys to be inserted into slots, a spring-loaded detent, or other known locking devices. In FIG. 2, the cannulated hub 200 is held in the first or second configuration by a spring assembly 130/132, such as a wave spring, for example. A key stock 128 locks the cannulated hub 200 in the first or second configuration.

Figure 3:
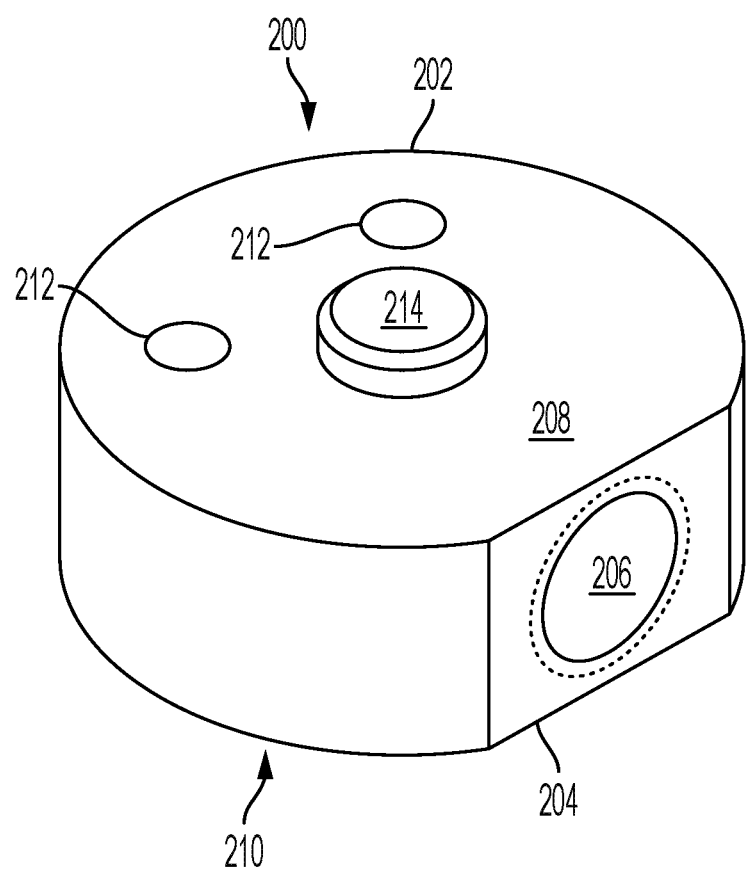
FIG. 3 is a close-up view schematic representation of a cannulated hub, according to an embodiment.

Turning now to FIG. 3, there is shown a close-up perspective view schematic representation of a cannulated hub 200, according to an embodiment. In the depicted embodiment, the cannulated hub 200 has a circular side 202 and one flat side 204. The flat side 204 comprises a threaded aperture 206 extending at least partially through the cannulated hub 200. The threaded aperture 206 is sized or otherwise configured to receive the driver shaft 300 (FIG. 1). The cannulated hub 200 has a first surface 208 and a second surface 210 with the circular side 202 and the flat side 204 extending therebetween. The first surface 208 comprises one or more detent features 212. In the depicted embodiment, the first surface 208 comprises two detent features 212. The detent features 212 are located on the first surface 208 such that they correspond to the threaded aperture 206 aligned with the first channel 114 and the second channel 116. In other words, the location of the detent features 212 on the first surface 208 of the cannulated hub 200 depend on the desired configurations of the driver shaft 300 and the positioning of the first and second channels 114, 116 (e.g., the first channel 114 extends at 90 degrees from the second channel 116). Both the first surface 208 and the second surface 210 of the cannulated hub 200 also comprise one or more central features 214 extending therefrom. The central features 214 interact with the first piece 108 and second piece 110, respectively, of the elongated body 102. The interactions between the central features 214 and the first and second pieces 108, 110 of the elongated body 102 allow the driver shaft 300 to rotate about the axis of the central features 214.

Figure 4:
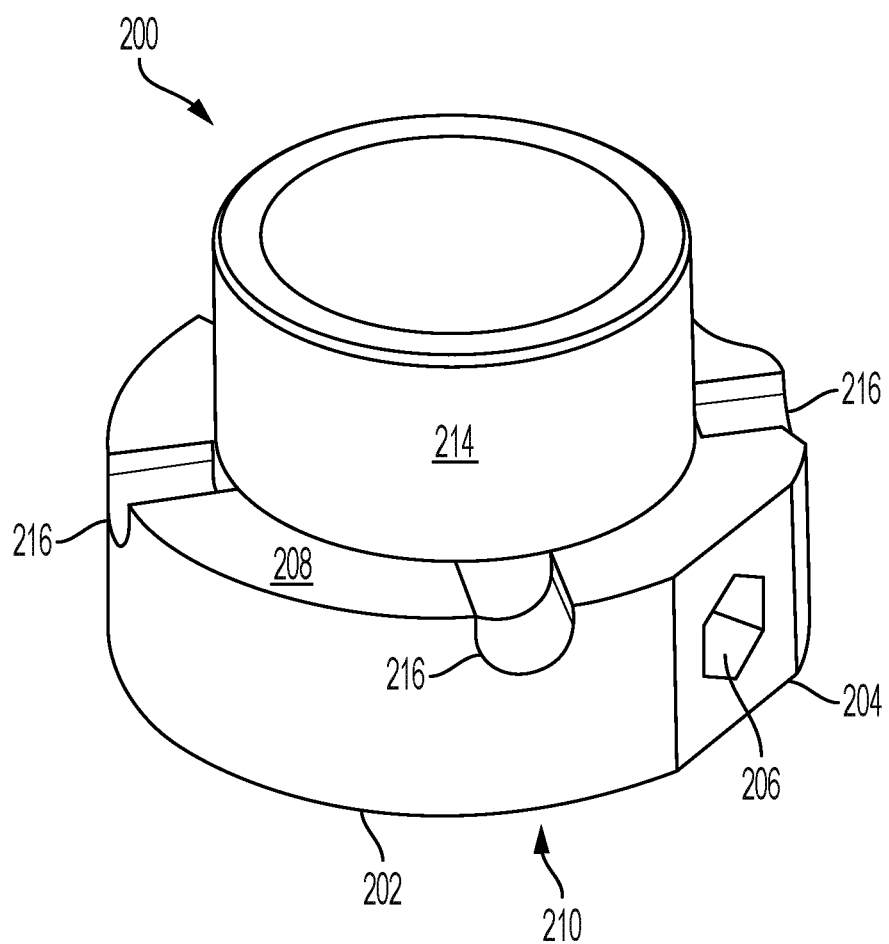
FIG. 4 is a close-up view schematic representation of a cannulated hub, according to an alternative embodiment.
Figure 6:
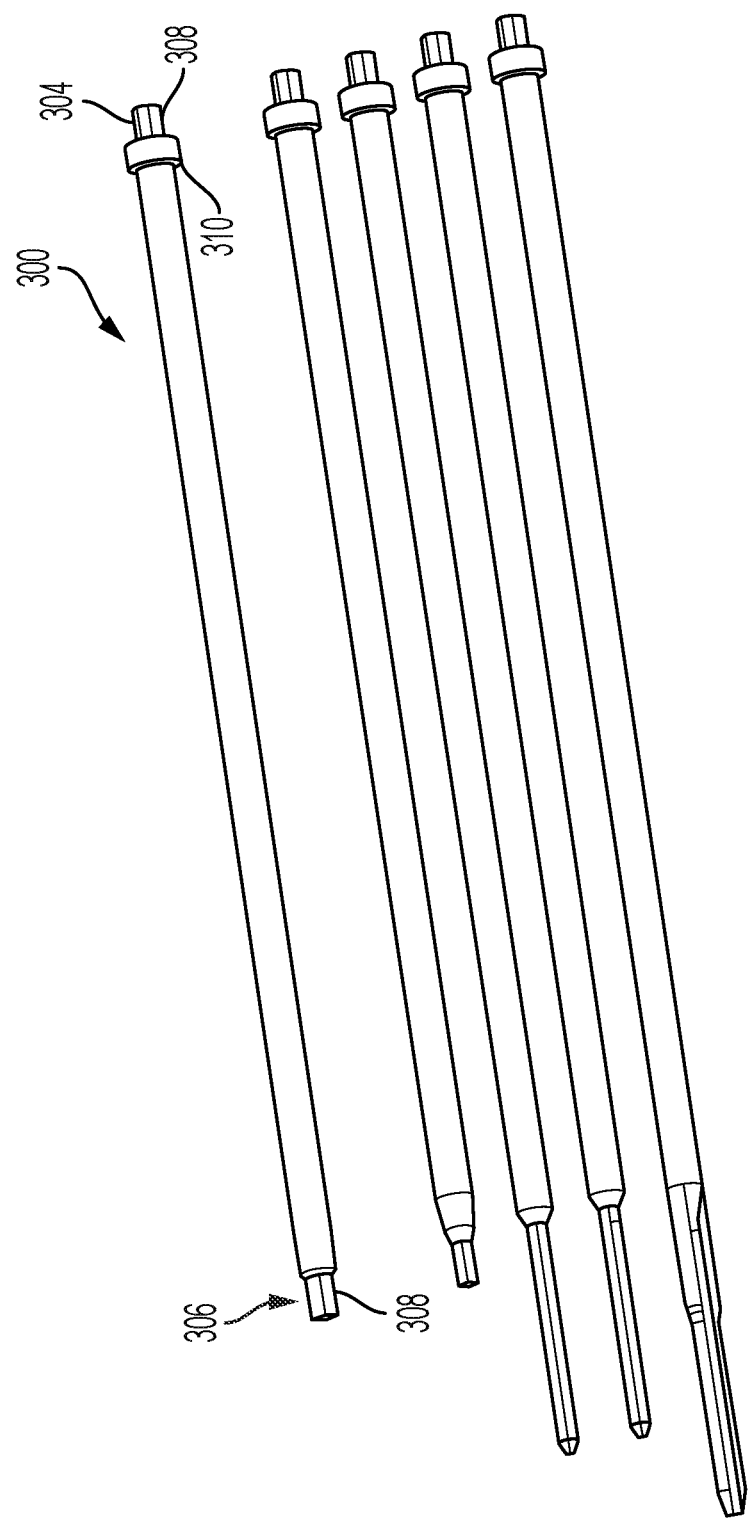
FIG. 6 is a perspective view schematic representation of a variety of driver shafts, according an alternative embodiment.
Figure 20:
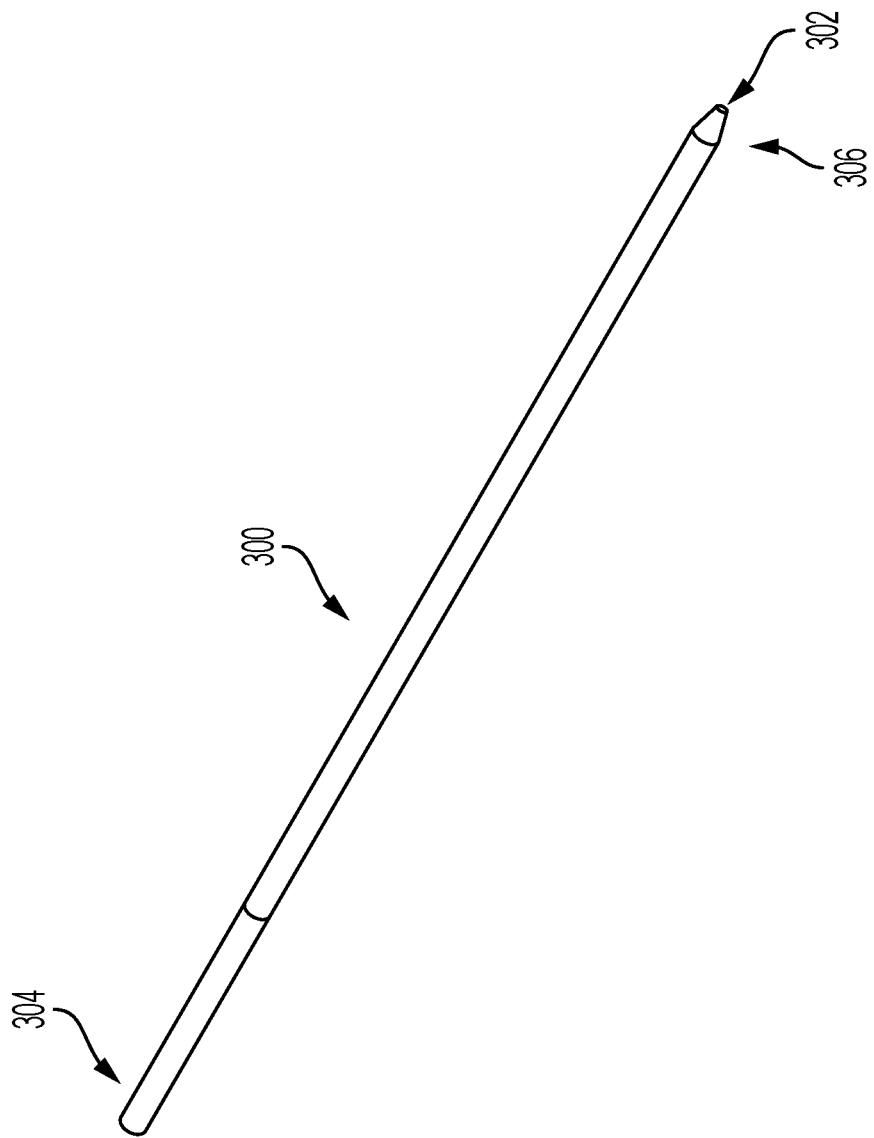
FIG. 20 is a perspective view schematic representation of an obturator shaft, according to an embodiment.

An alternative embodiment of the cannulated hub 200 is shown in FIG. 4. The cannulated hub 200 in FIG. 4 also has a first surface 208 and a second surface 210 with a circular side 202 and one flat side 204 extending therebetween. However, in the embodiment shown in FIG. 4, the aperture 206 extending at least partially through the flat side 204 of the cannulated hub 200 is a geometric aperture 206. The geometric aperture 206 is shaped, sized, or otherwise configured to receive a driver geometry 308 at a locking end 304 of a driver shaft 300 (FIG. 6/FIG. 20). The cannulated hub 200 in FIG. 4 also has a first surface 208 and a second surface 210 with a circular side 202 and one flat side 204 extending therebetween. As shown, the first surface has one or more slot features 216 extending from the circular side 202 through at least a portion of the first surface 208. The slot features 216 lock the driver shaft 300 in the first and second configurations. The slot features 216 extend through the first surface 208 up to the central feature 214. In the depicted embodiment, there are four slot features 216. The number of slot features 216 can vary based on a number of factors, such as the relative positioning of the first and second channels 114, 116 and the desired degree of rotation of the driver shaft 300. In addition, the location of the slot features 216 on the first surface 208 of the cannulated hub 200 depend on the desired configurations of the driver shaft 300 and the positioning of the first and second channels 114, 116 (e.g., the first channel 114 extends at 90 degrees from the second channel 116).

Figure 5:
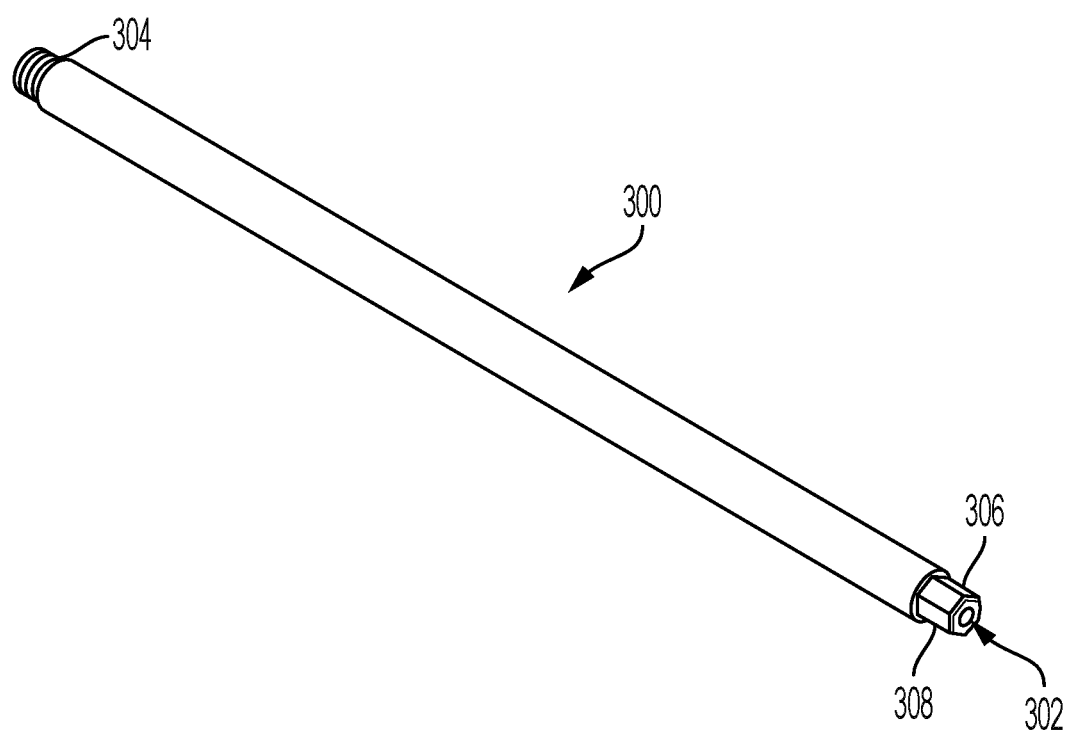
FIG. 5 is a perspective view schematic representation of a driver shaft, according to an embodiment.

Referring briefly to FIG. 5, there is shown a perspective view schematic representation of a driver shaft 300, according to an embodiment. In the depicted embodiment, the driver shaft 300 is a cannulated driver shaft 300 (i.e. with a lumen 302 extending therethrough). The driver shaft 300 has a threaded locking end 304 which is configured to mate with or otherwise engage with the threaded aperture 206 (FIG. 3) to secure the driver shaft 300 within the cannulated hub 200. The driver shaft 300 in FIG. 5 also has an opposing driving end 306. As shown, the driving end 306 has a driver geometry 308 to transmit torque. The driver geometry 308 can be hex, torque, or any other geometry required to properly transmit torque to a fastener (e.g., screw).

In an alternative embodiment of the driver shaft 300 shown in FIG. 6, the driver shaft 300 comprises driver geometry 308 at the locking end 304 to mate or otherwise engage with the geometric aperture 206 on the flat side 204 of the cannulated hub 200. As with the embodiment described above and shown in FIG. 5, the driver shaft 300 of FIG. 6 includes the driver geometry 308 at the driving end 306. The driver geometry 308, at the locking end 304 and the driving end 306, can be hex, torque, or any other geometry required to properly transmit torque to a fastener (e.g., screw). Also in the embodiment of FIG. 6, the driver shaft 300 can include a driver locking feature 310, which locks into the elongated body 102. In the depicted embodiment, the driver locking feature 310 is a ring extending around the driver shaft 300 and abutting the locking end 304 of the driver shaft 300. The driver shaft 300 locks into the elongated body 102 in each of the first and second configurations. The elongated body 102 allows for the driver shafts 300 to be interchanged when the cannulated hub 200 is rotated from the first configuration to the second configuration.

Figure 7A:
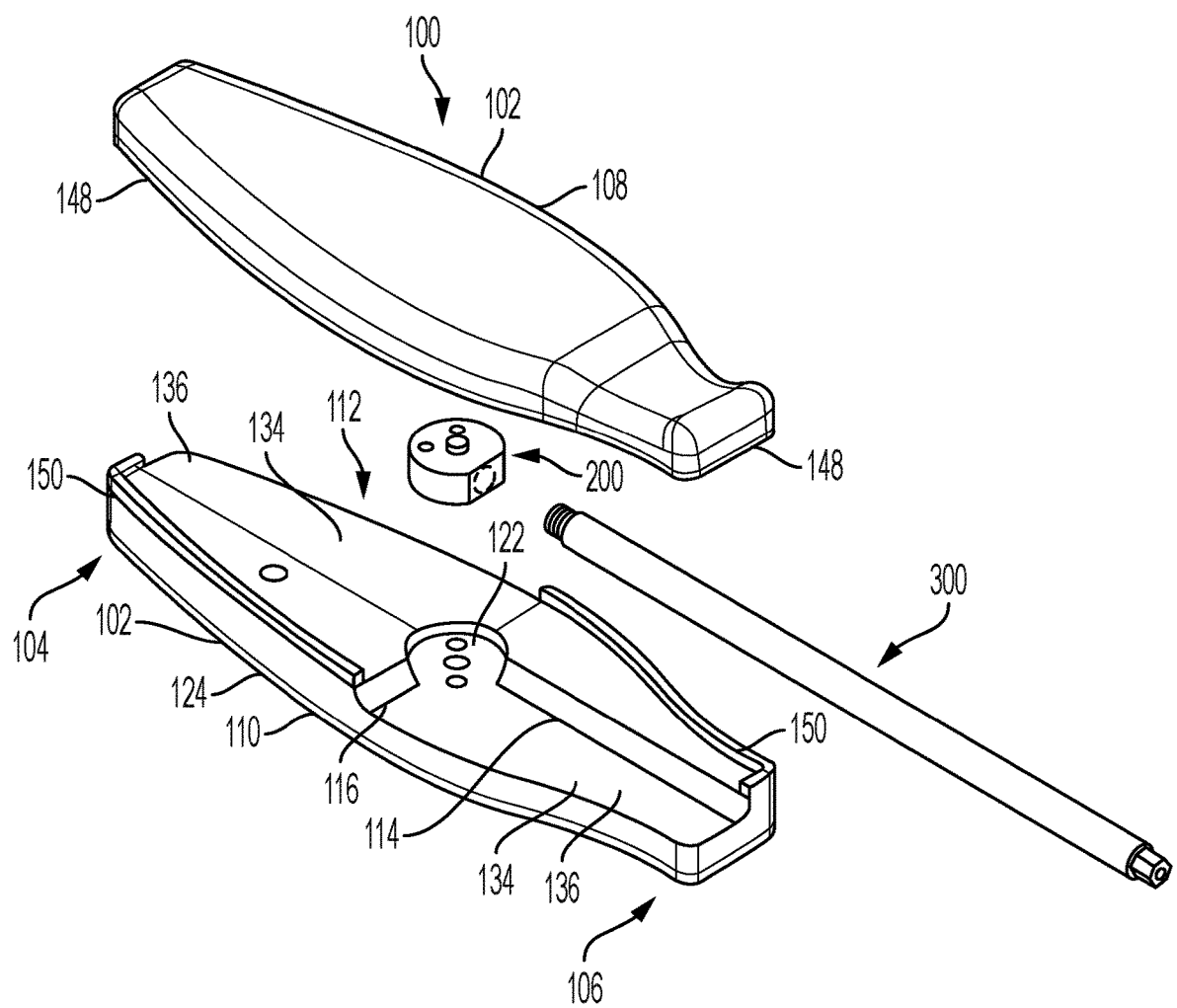
FIG. 7A is an exploded view schematic representation of a driver assembly with a relief area, according to an embodiment.
Figure 7B:
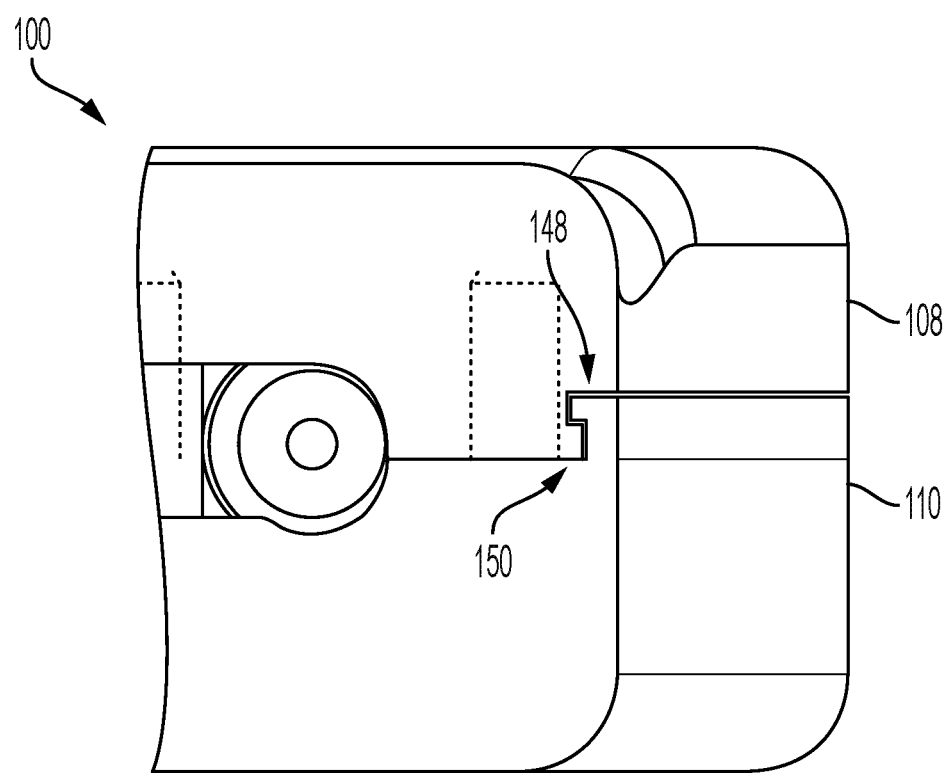
FIG. 7B is a close-up view schematic representation of interfacing flanges on the first and second pieces of the driver assembly, according to an embodiment.

Turning to FIG. 7A, there is shown another exploded view schematic representation of the driver assembly 100, according to an embodiment. In the depicted embodiment, the elongated body 102 comprises one or more relief areas 134 for a guide pin (not shown) and the driver shaft 300. The relief areas 134 provide an uninterrupted space for the guide pin as the driver shaft 300 rotates between the first channel 114 and the second channel 116. In the depicted embodiment, a relief area 134 (a quadrant stepped down from at least one other quadrant, where the channels 114, 116 are further stepped down) is on an inner surface 136 of the second piece 110. The first and second pieces 108, 110 each comprise a flange (or lip) 148, 150, wherein the flanges 148, 150 are configured to align and lock together, as shown in FIG. 7B, overcoming the spring force of the cannulated hub 200 while the driver assembly 100 is fastened together during manufacturing. The interfacing flanges 148, 150 also prevent the first and second pieces 108, 110 from breaking apart or otherwise separating when the driver shaft 300 rotates between the first and second channels 114, 116. The flanges 148, 150 also simplify manufacturing by reducing the number of fasteners of the driver assembly 100.

Figure 8:
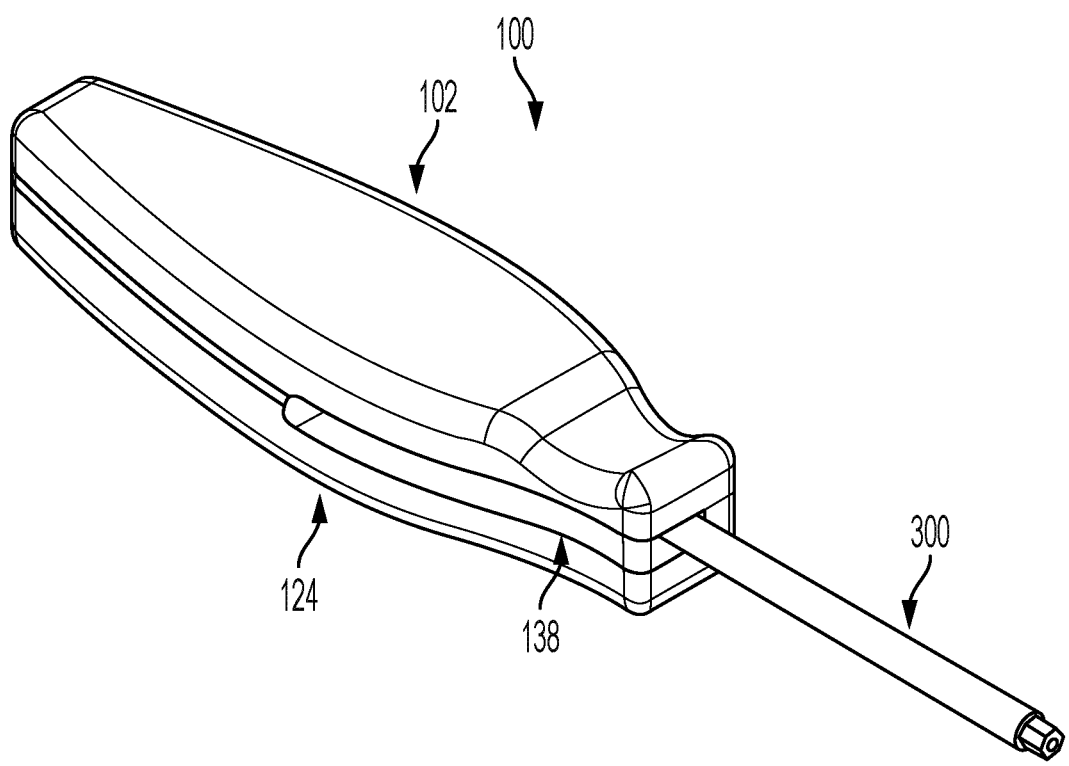
FIG. 8 is a perspective view schematic representation of a driver assembly in the first configuration, according to an embodiment.
Figure 9:
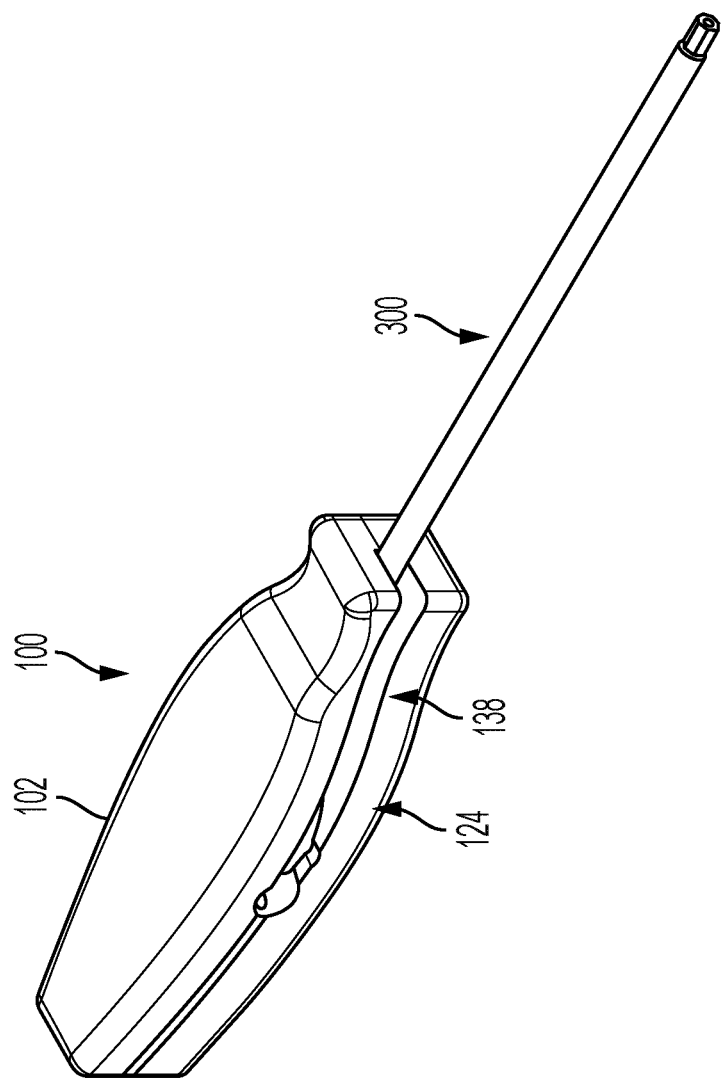
FIG. 9 is a perspective view schematic representation of a driver assembly in the first configuration, according to an alternative embodiment.
Figure 10:
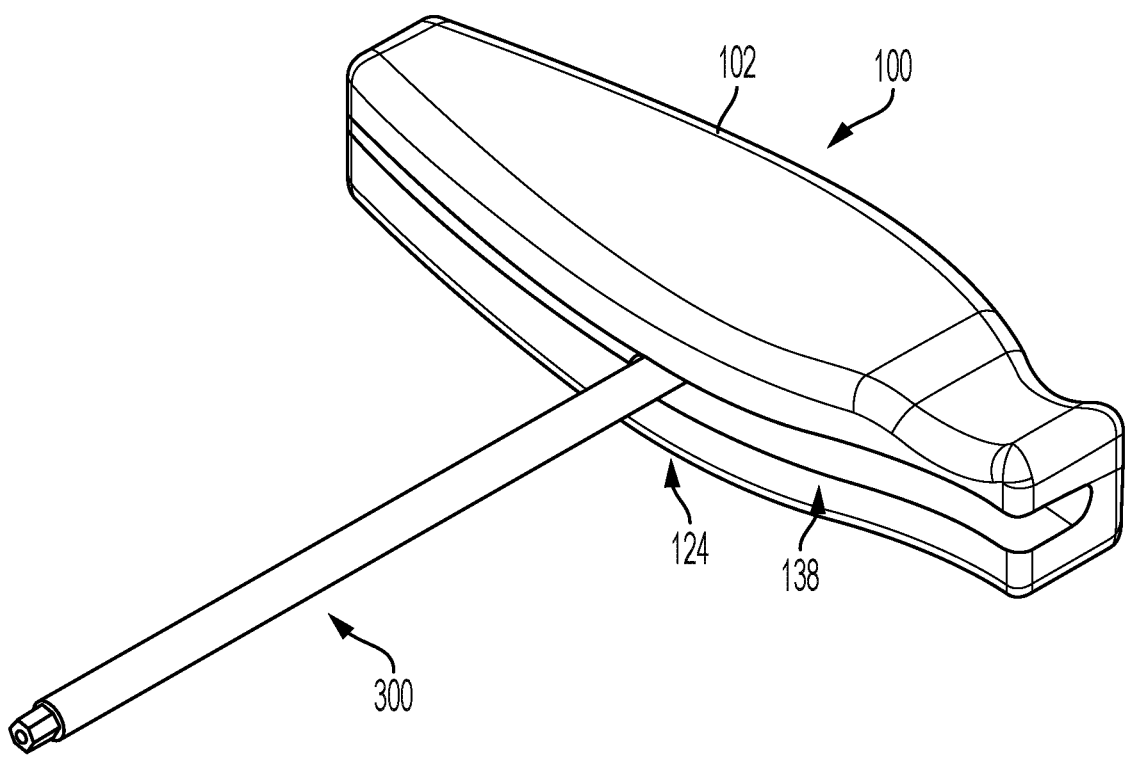
FIG. 10 is a perspective view schematic representation of a driver assembly in the second configuration, according to an embodiment.
Figure 11:
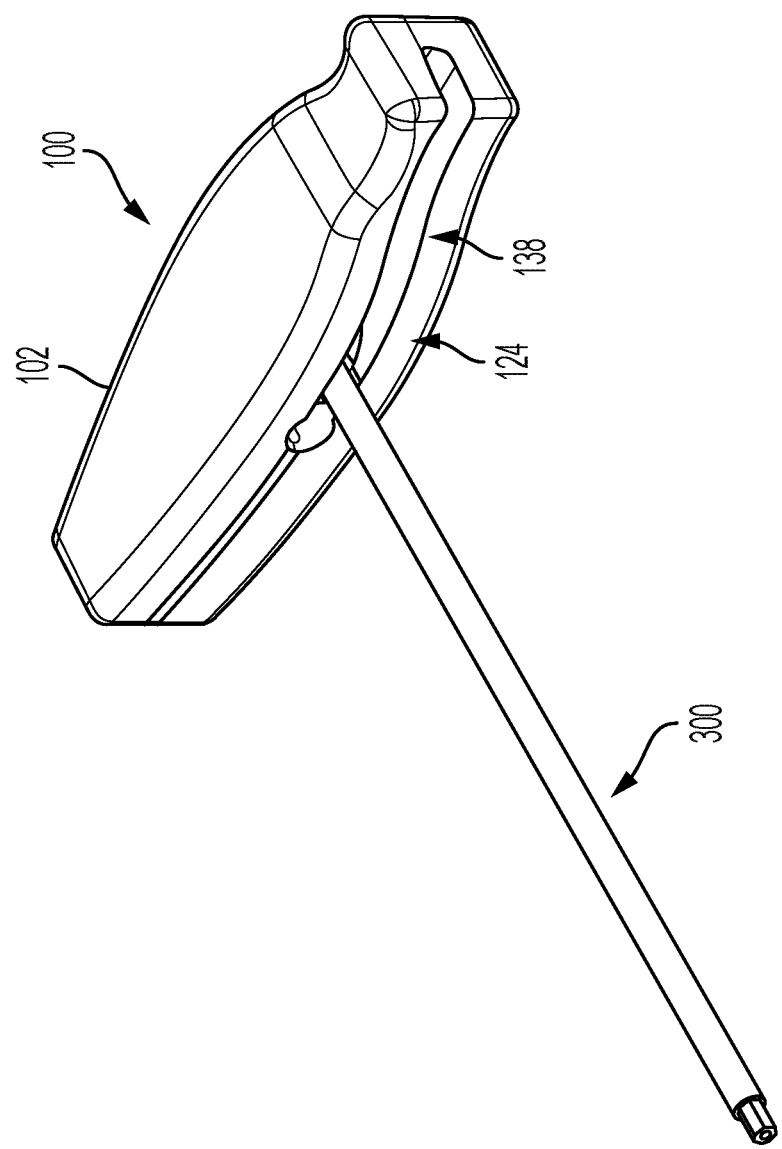
FIG. 11 is a perspective view schematic representation of a driver assembly in the second configuration, according to an alternative embodiment.

Referring now to FIGS. 8-9 and 10-11, there are shown perspective views schematic representations of the driver assembly 100 in the fully assembled first configuration and the second configuration, respectively, according to embodiments. As shown in FIGS. 8-9, in the first configuration, the driver shaft 300 extends through the first channel 114 in the elongated body 102 and out through the distal end 106 of the elongated body 102. The driver shaft 300 is then rotated via the cannulated hub 200 through a first slot 138 (or other space) in the first side 124 of the elongated body 102 between the first piece 108 and second piece 110 to the second channel 116 in order to achieve the second configuration. FIGS. 10-11 show the driver shaft 300 extending through the second channel 116 in the elongated body 102 and out through the first side 124 of the elongated body 102. In embodiments depicted in FIGS. 8-11, the driver shaft 300 rotates 90 degrees between the first configuration (FIGS. 8-9) and the second configuration (FIGS. 10-11).

Figure 12:
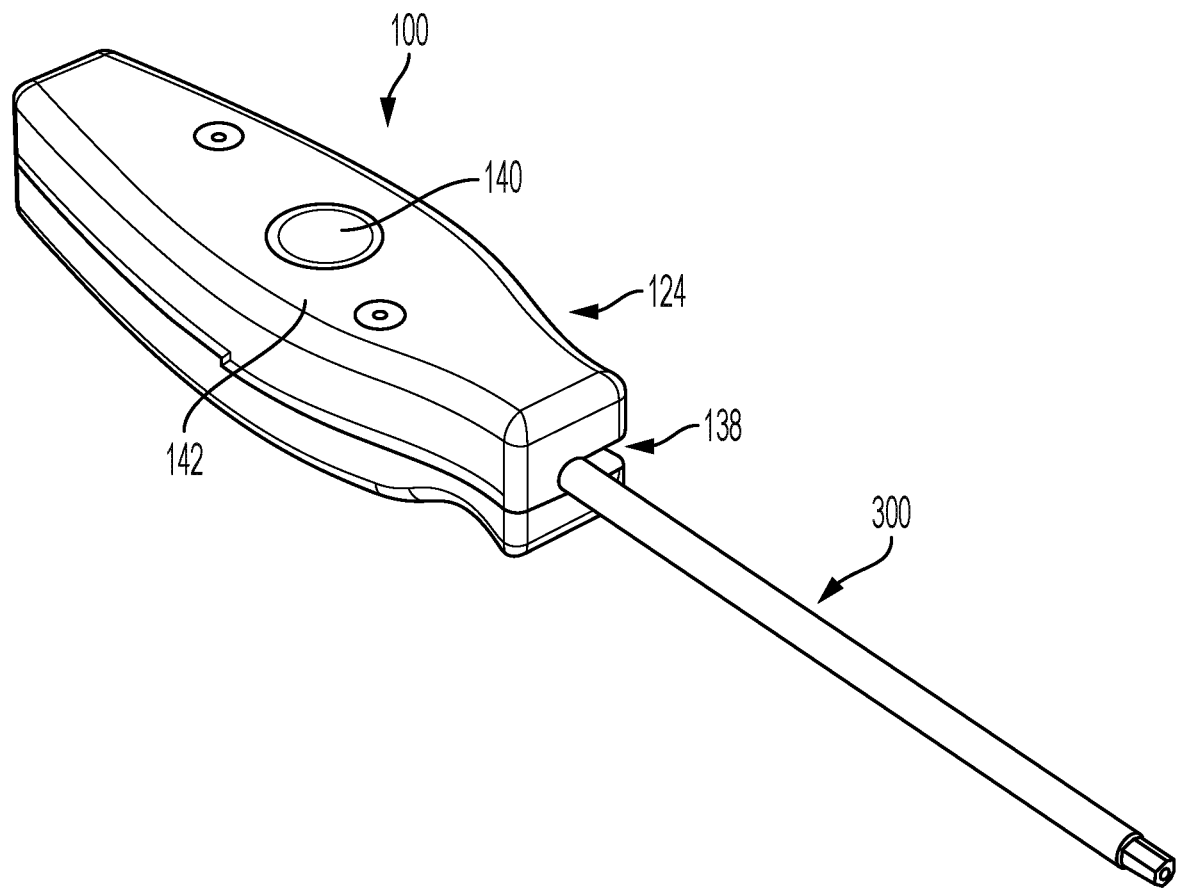
FIG. 12 is a perspective view schematic representation of a driver assembly with an actuator, according to an alternative embodiment.

An alternative embodiment of the driver assembly 100 in the first configuration is shown in FIG. 12. The elongated body 102 comprises an actuator 140 for rotating the driver shaft 300. In the depicted embodiment, the actuator 140 is a button on an outer surface 142 of the first piece 108 of the elongated body 102. By engaging the button 140, the spring assembly 130/132 (coupled thereto) holding the cannulated hub 200 in either the first or second configuration is depressed to allow for rotation (automatic via a biasing member/spring, or via manual actuation) of the driver shaft 300 between the first and second configuration.

Figure 13:
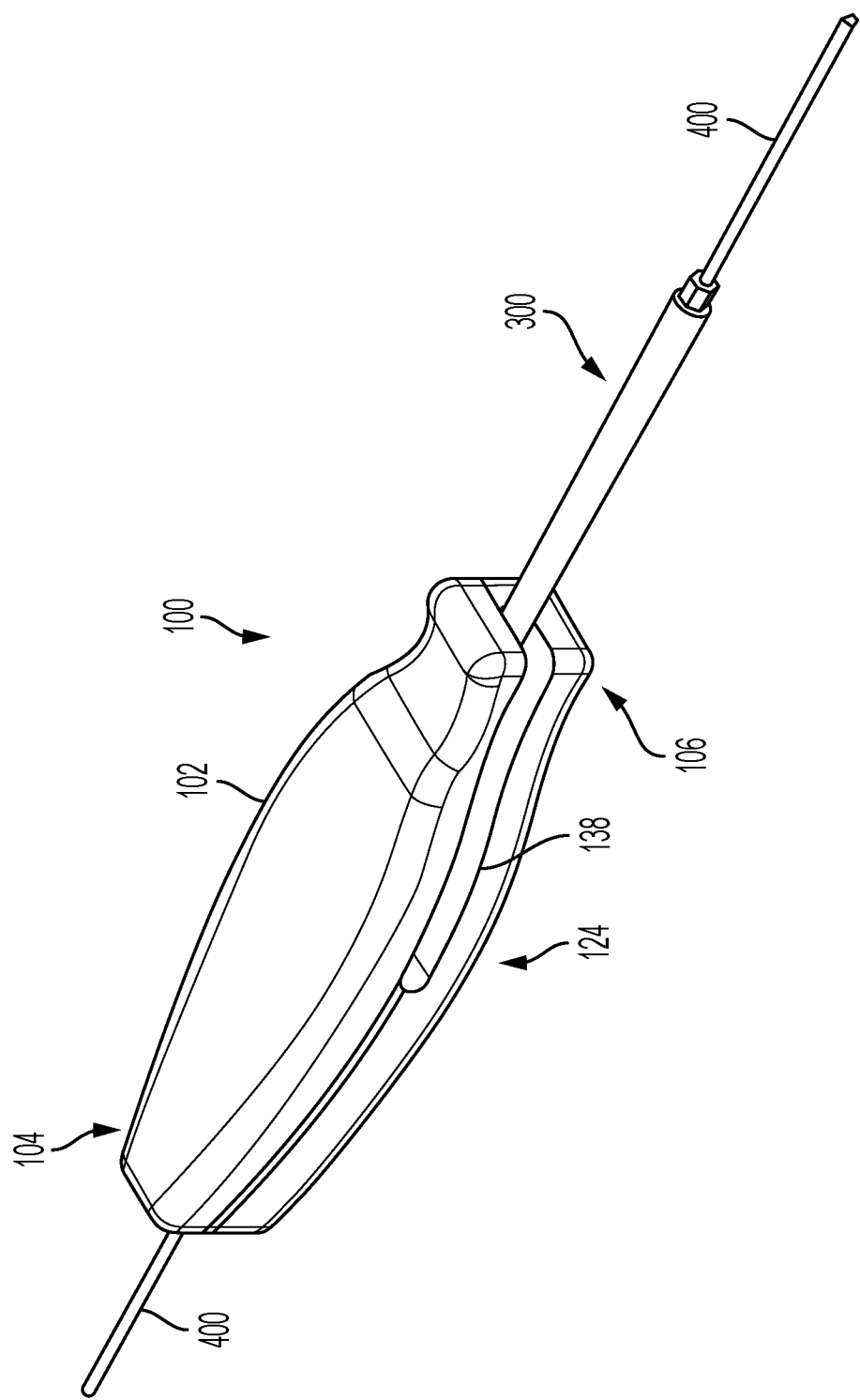
FIG. 13 is a perspective view schematic representation of a driver assembly in the first configuration with a guide pin extending therethrough, according to an embodiment.
Figure 14:
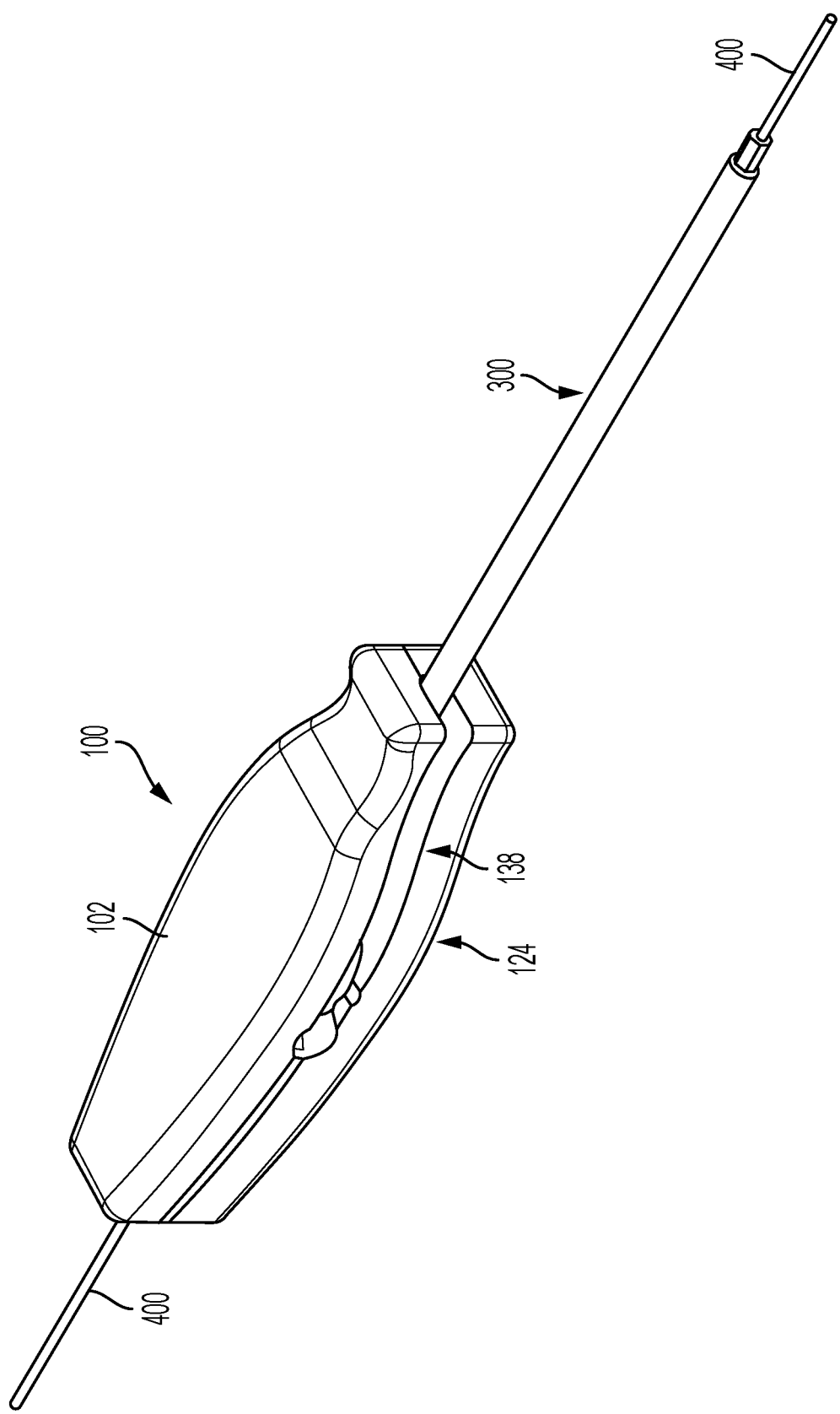
FIG. 14 is a perspective view schematic representation of a driver assembly in the first configuration with a guide pin extending therethrough, according to an alternative embodiment.
Figure 15:
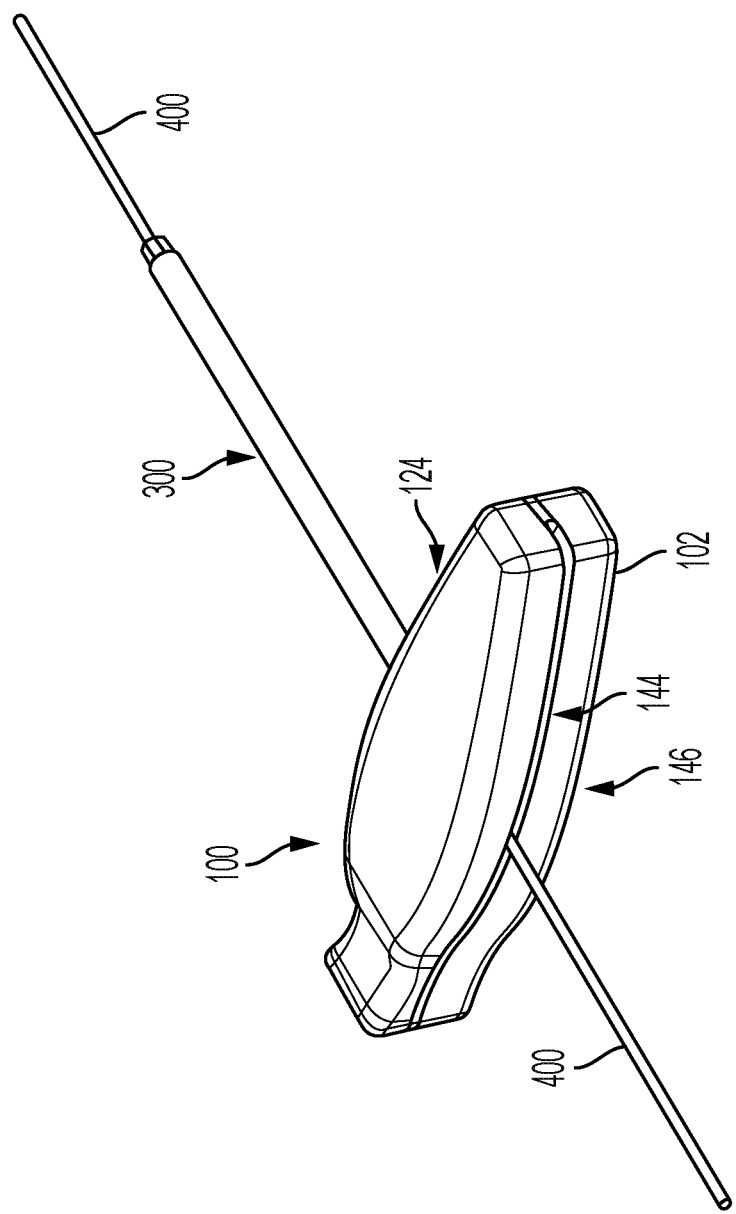
FIG. 15 is a perspective view schematic representation of a driver assembly in the second configuration with a guide pin extending therethrough, according to an embodiment.
Figure 16:
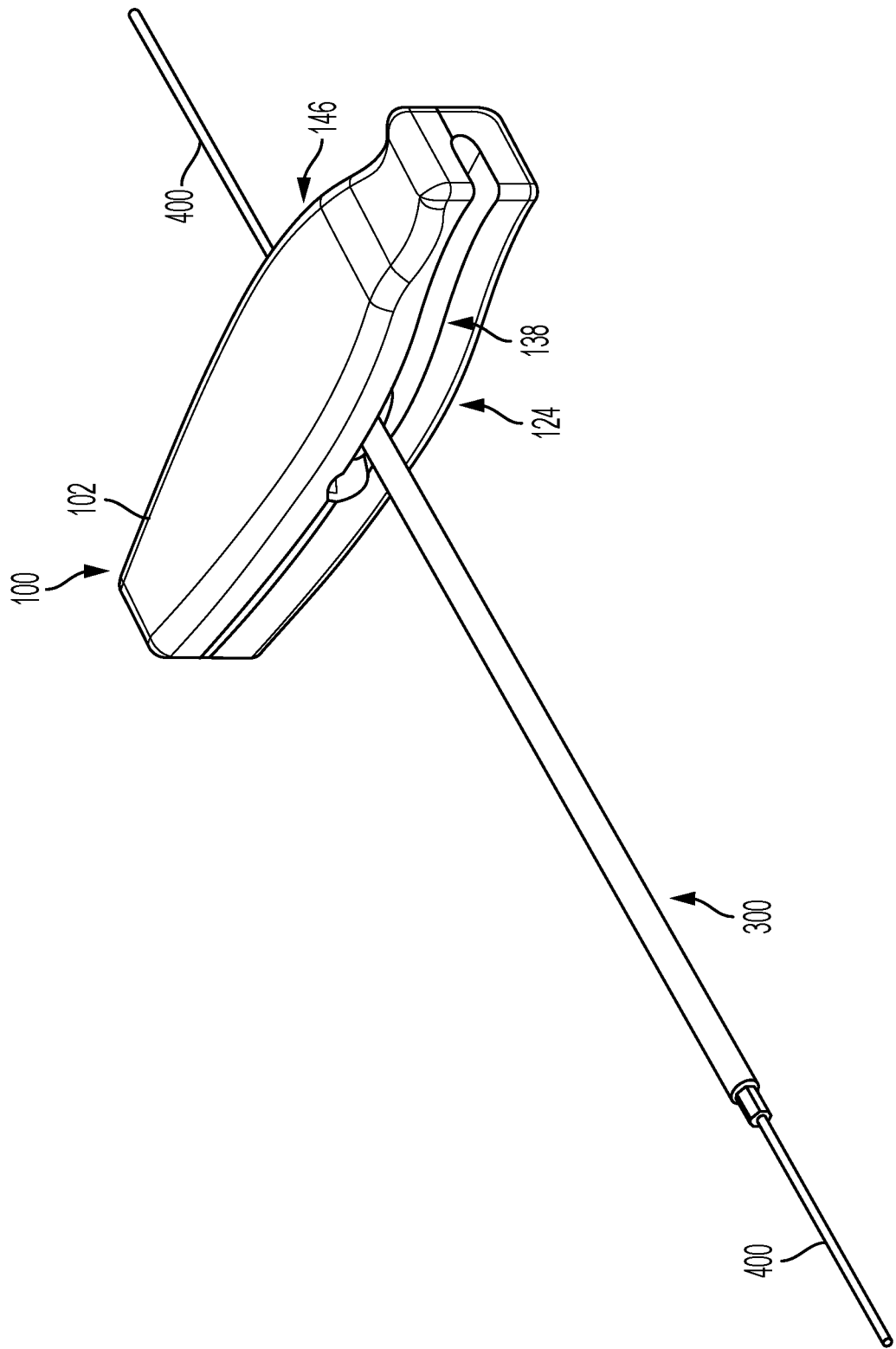
FIG. 16 is a perspective view schematic representation of a driver assembly in the second configuration with a guide pin extending therethrough, according to an alternative embodiment.
Figure 17:
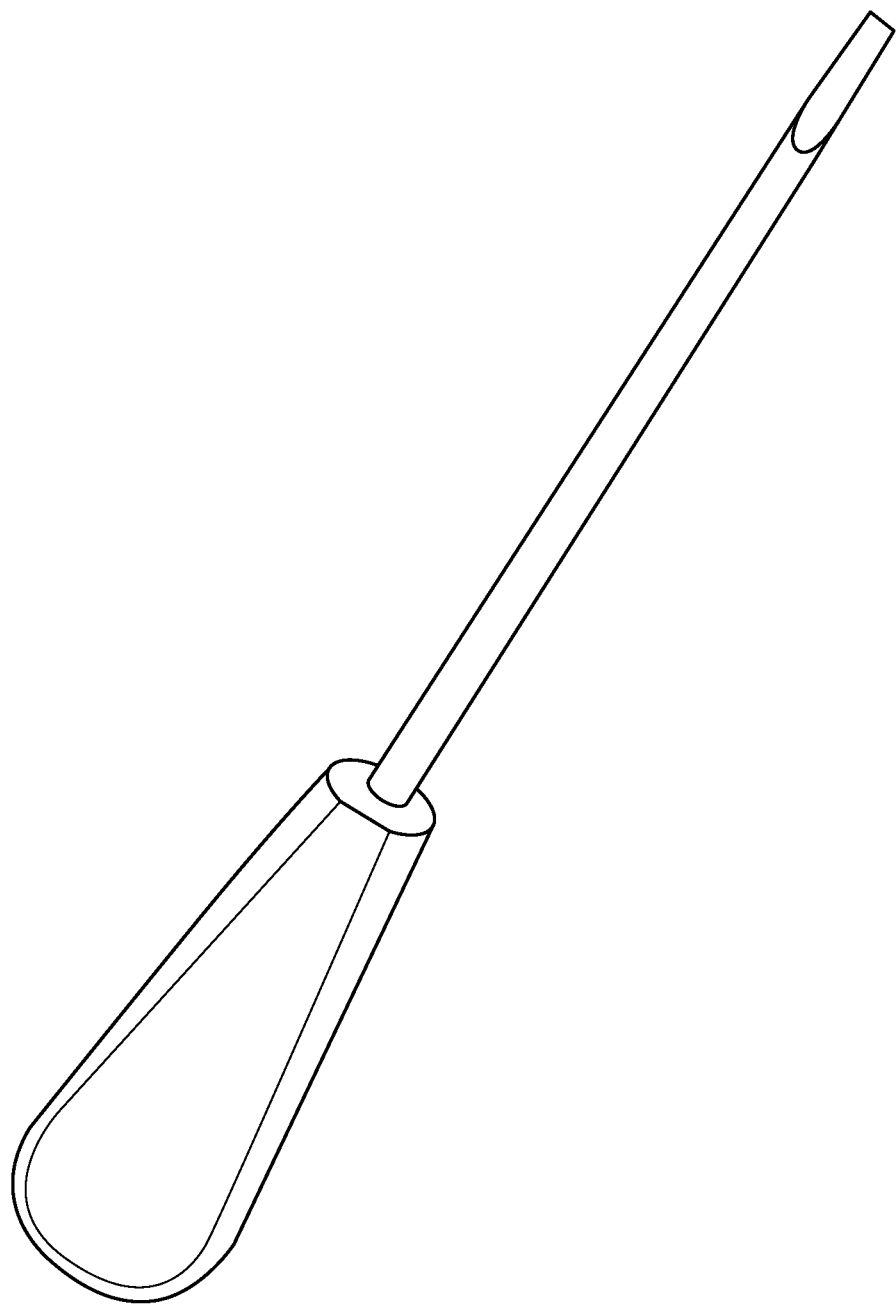
FIG. 17 is a perspective view of a driver of the prior art.
Figure 18:
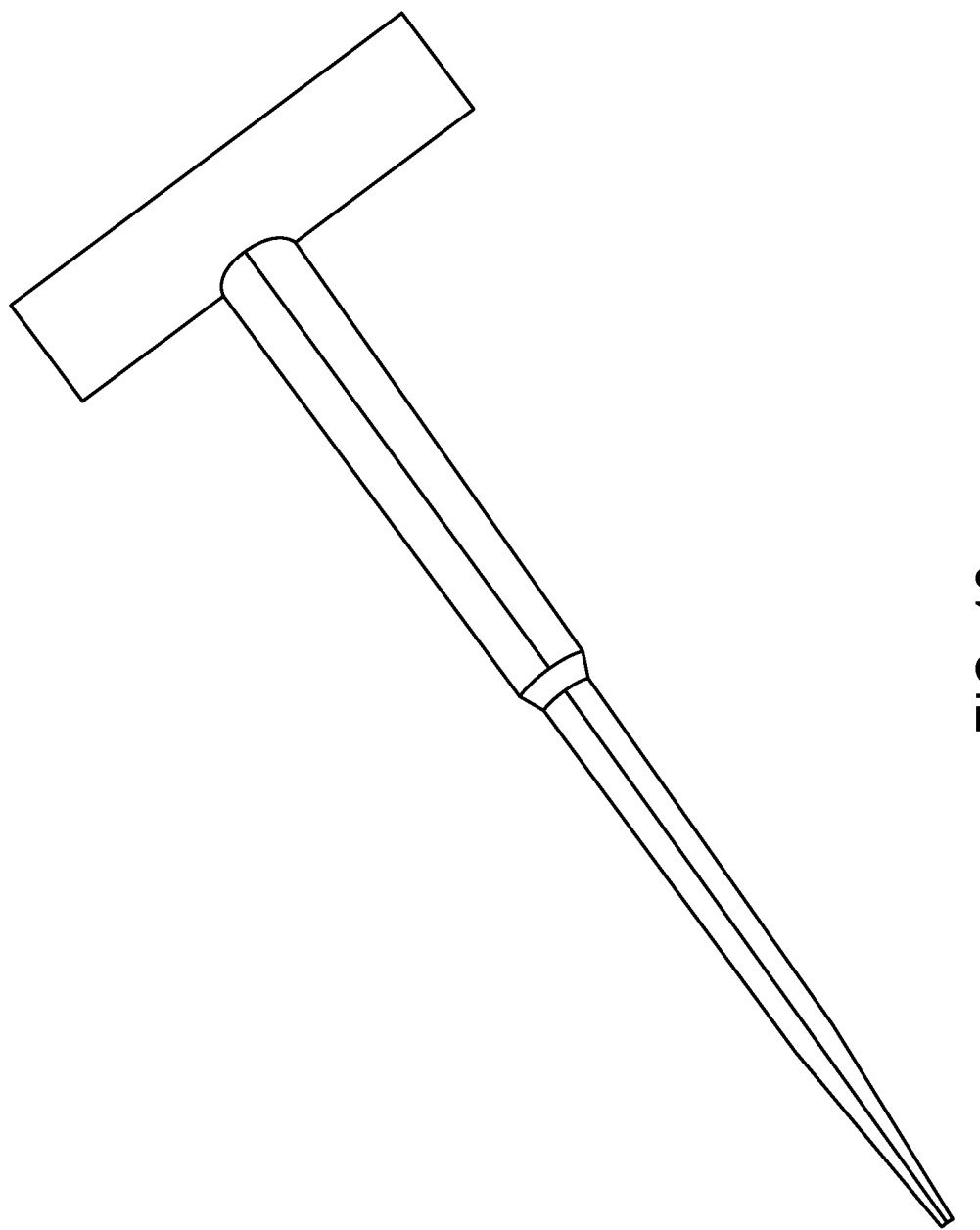
FIG. 18 is a perspective view of another driver of the prior art.

Turning to FIGS. 13-14 and 15-16, there are shown perspective views schematic representations of the driver assembly 100 in the first configuration and the second configuration, respectively, with a guide pin 400 inserted therethrough, according to embodiments. As shown in FIGS. 13-14, in the first configuration, a guide pin 400 is inserted through the proximal end 104 of the elongated body 102 and into the lumen 302 of the cannulated driver shaft 300. As the driver shaft 300 extends through the first channel 114 and out through the distal end 106 of the elongated body 102 in the first configuration, the guide pin 400 also extends out of the distal end 106 of the elongated body 102. The driver shaft 300 and guide pin 400 are then rotated via the cannulated hub 200 to achieve the second configuration shown in FIGS. 15-16. Upon rotation of the driver shaft 300 through the first slot 138, the guide pin 400 rotates through a second slot 144 between the first piece 108 and second piece 110 of the elongated body 102 on a second side 146 of the elongated body 102. FIGS. 15-16 shows the guide pin 400 extending through the second slot 144 on the second side 146 of the elongated body 102 through the driver shaft 300 (in the second channel 116) and out through the first side 124 of the elongated body 102. In embodiment depicted in FIGS. 13-16, the driver shaft 300 and guide pin 400 rotate 90 degrees between the first configuration (FIGS. 13-14) and the second configuration (FIGS. 15-16).

Figure 19:
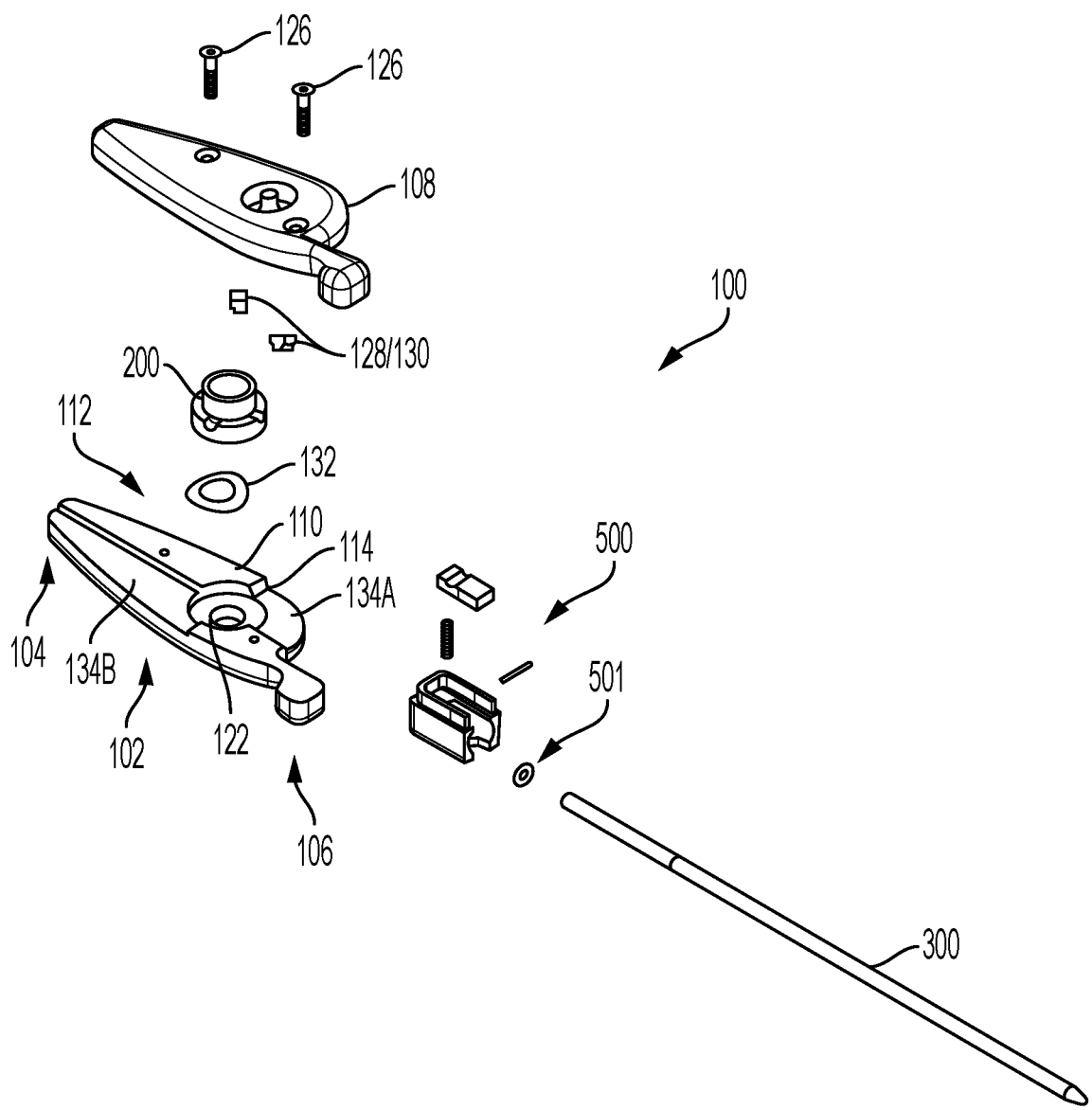
FIG. 19 is an exploded view schematic representation of an obturator assembly, according to an embodiment.

Referring now to some additional figures, wherein like reference numerals refer to like parts throughout (and references to similar features/components as discussed with respect to FIGS. 1-18, are the same or similar with reference to the following non-prior art FIGS.), FIG. 19 shows an exploded view schematic representation of an obturator assembly 100, according to an alternative embodiment. In the depicted embodiment, the obturator assembly 100 comprises an elongated body 102 extending between a proximal end 104 and a distal end 106. The elongated body 102 and any other component parts of the obturator assembly 100 can be composed of disposable or reusable material (as should be understood by a person of ordinary skill. Further, the obturator assembly 100 can be manufactured or otherwise assembled to prevent or allow disassembly. The elongated body 102 can be ergonomically designed to improve the grip of the user on the elongated body 102. In the embodiment shown in FIG. 19, the elongated body 102 comprises a first piece 108 and a second piece 110, both sized and configured to align and connect, forming an inner volume 112 of the elongated body 102.

Still referring to FIG. 19, the second piece 110 of the elongated body 102 comprises a first relief area 134A and a second relief area 134B extending partially therethrough. In the depicted embodiment, each relief area 134A, 134B is a quadrant stepped down from at least one other quadrant on an inner surface 136 of the second piece 110. The first and second relief areas 134A, 134B provide an uninterrupted space for a guide pin (not shown) as an obturator shaft 300 rotates. The first and second relief areas 134A, 134B converge at a central recess 122 in the second piece 110, as shown. In the depicted embodiment, the central recess 122 is a circular space stepped down from the first and second relief areas 134A, 134B.

The first relief area 134A additionally comprises a channel 114 extending therethrough. In the depicted embodiment, the channel 114 is also stepped down from the first relief area 134A and extends to the central recess 122. The channel 114 is sized and configured to accommodate the obturator shaft 300, so when the obturator shaft 300 rotates, it snaps or otherwise locks into the channel 114. The channel 114 is shallow such that obturator shaft 300 can be moved out of the channel 114 with force.

As shown in FIG. 19, one or more connectors 126 and accessories, such as screws, dowel pins, and o-rings, are used to connect the first piece 108 and the second piece 110 of the elongated body 102 as well as other components of the obturator assembly 100. A cannulated hub 200 is sized or otherwise configured to fit into the recess 122 within the second piece 110, and is configured to rotate the obturator shaft 300. The cannulated hub 200 is rotatable within the recess 122 via a locking mechanism 128. The locking mechanism 128 can be used to hold the obturator shaft 300 in the first configuration and/or in the second configuration with a predetermined force that can be overcome with relatively low force (automatic spring action, or manual user actuation) to allow the obturator shaft 300 to rotate about the cannulated hub 200.

In the depicted embodiment, the locking mechanism 128 is a spring-loaded detent; however, alternative similar connectors may be used (as should be understood by a person or ordinary skill in the art in conjunction with a review of this disclosure). In an alternative embodiment, the locking mechanism 128 can be one or more keys to be inserted into slots, a spring-loaded detent, or other known locking devices. In FIG. 19, the cannulated hub 200 is held in the first or second configuration by a spring assembly 130/132, such as a wave spring, for example. A key stock 128 locks the cannulated hub 200 in the first or second configuration.

Referring briefly to FIG. 20, there is shown a perspective view schematic representation of an obturator shaft 300, according to an embodiment. In the depicted embodiment, the obturator shaft 300 is a cannulated driver shaft (i.e. with a lumen 302 extending therethrough). The obturator shaft 300 in FIG. 20 has a locking end 304 sized and configured to mate with or otherwise engage the cannulated hub 200 (e.g., at the geometric aperture 206 on the flat side 204 shown in FIG. 3). The obturator shaft 300 also has an opposing smooth, tapered end 306. The obturator shaft 300 can have a uniform diameter from the locking end 304 up to start of the tapering of the tapered end 306 or the obturator shaft 300 can have multiple (or varying) diameters along its length. The diameter of the obturator shaft 300 may also be optimized to accommodate a cannula of a certain size.

Figure 21:
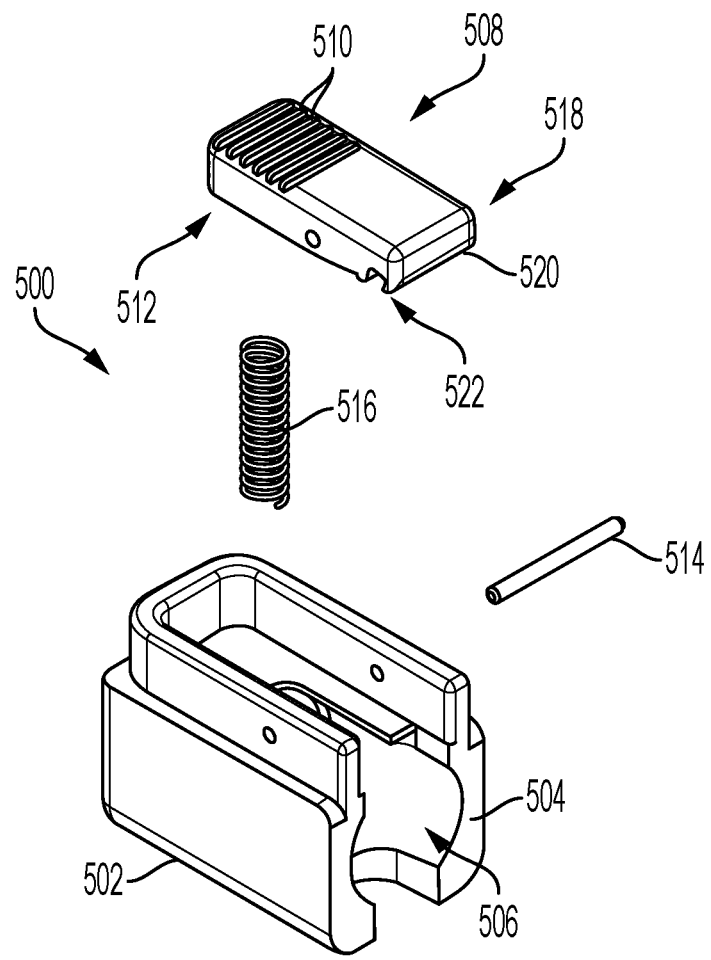
FIG. 21 is an exploded view schematic representation of a latch assembly, according to an embodiment.

Turning to FIG. 21, there is shown an exploded view schematic representation of a latch assembly 500, according to an embodiment. As shown in FIG. 19, the latch assembly 500 is connected to the obturator shaft 300 via conventional connectors and components, including, in some instances, an o-ring 501. As depicted in FIG. 21, the latch assembly 500 comprises a latch sheath 502. The latch sheath 502 composes the body of the latch assembly 500 and is rectangular in the depicted embodiment. The latch sheath 502 comprises an open end 504 for receiving the obturator shaft 300 (FIG. 19). A channel 506 extends from the open end 504 and through the latch sheath 502 such that the obturator shaft 300 may extend therethrough to the cannulated hub 200.

Still referring to FIG. 21, the latch assembly 500 further comprises a latch 508. The latch 508 is a movable actuator connected to the latch sheath 502. In the depicted embodiment, the latch 508 is rectangular and comprises a set of ridges 510 on its proximal end 512 to optimize the grip of the user. The latch 508 is connected to the latch sheath 502 via connectors, such as the pin 514 shown in FIG. 21. The pin 514 connects the latch 508 to the latch sheath 502 with a spring 516 therebetween. In a relaxed state, the spring 516 pushes up against the proximal end 512 of the latch 508. This pushes a distal end 518 of the latch 508 downward toward the channel 506 (and obturator shaft 300 (FIG. 19)).

When the user applies force to the latch 508 by pressing down on the proximal end 512, the distal end 518 of the latch 508 rotates or moves upward, away from the channel 506 (and obturator shaft 300 (FIG. 19)). In the depicted embodiment, the distal end 518 of the latch 508 comprises a flange 520, creating a hook or channel 522 extending along the distal end 518 of the latch 508. The flange 520 and the channel 522 are configured to grab or otherwise lock onto a component extending into the open end 504 of the latch sheath 508, as described in detail below.

Figure 22:
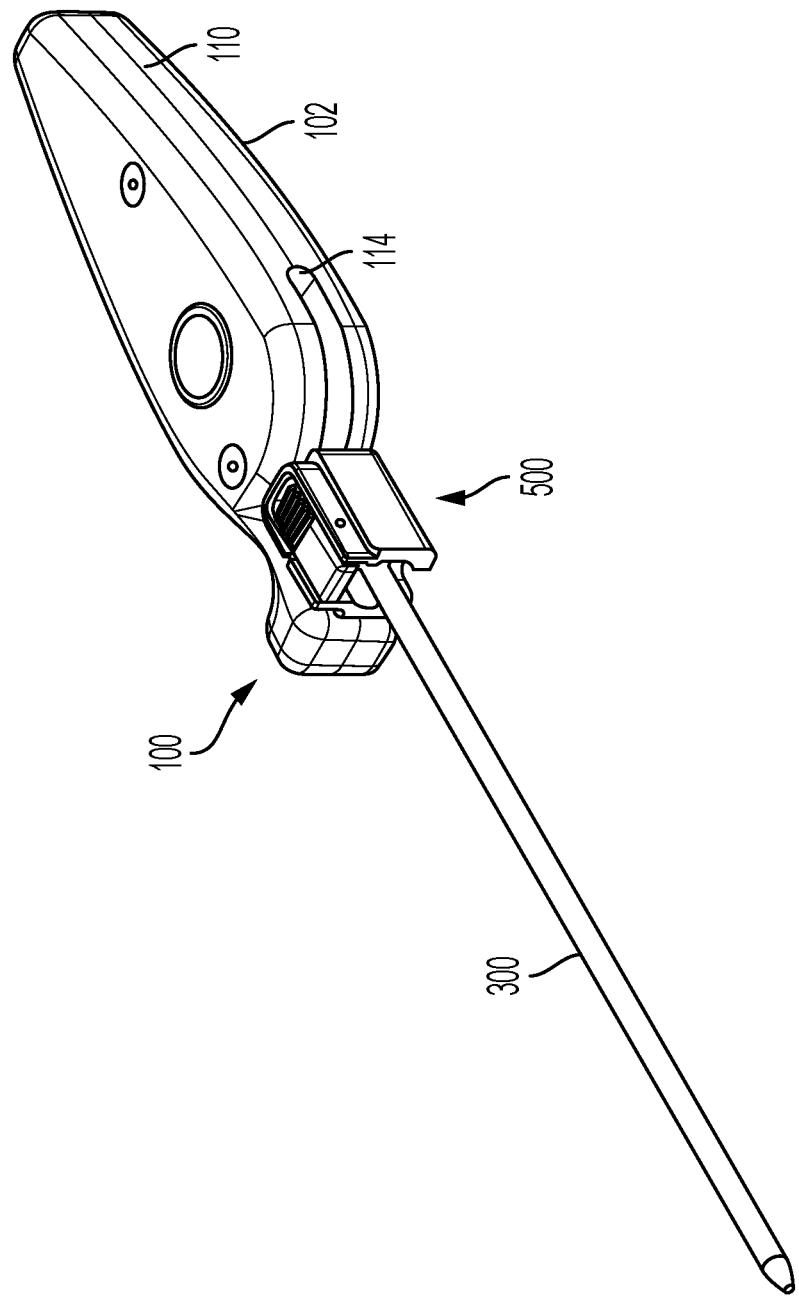
FIG. 22 is a perspective view schematic representation of an obturator assembly in the first configuration, according to an embodiment.
Figure 23:
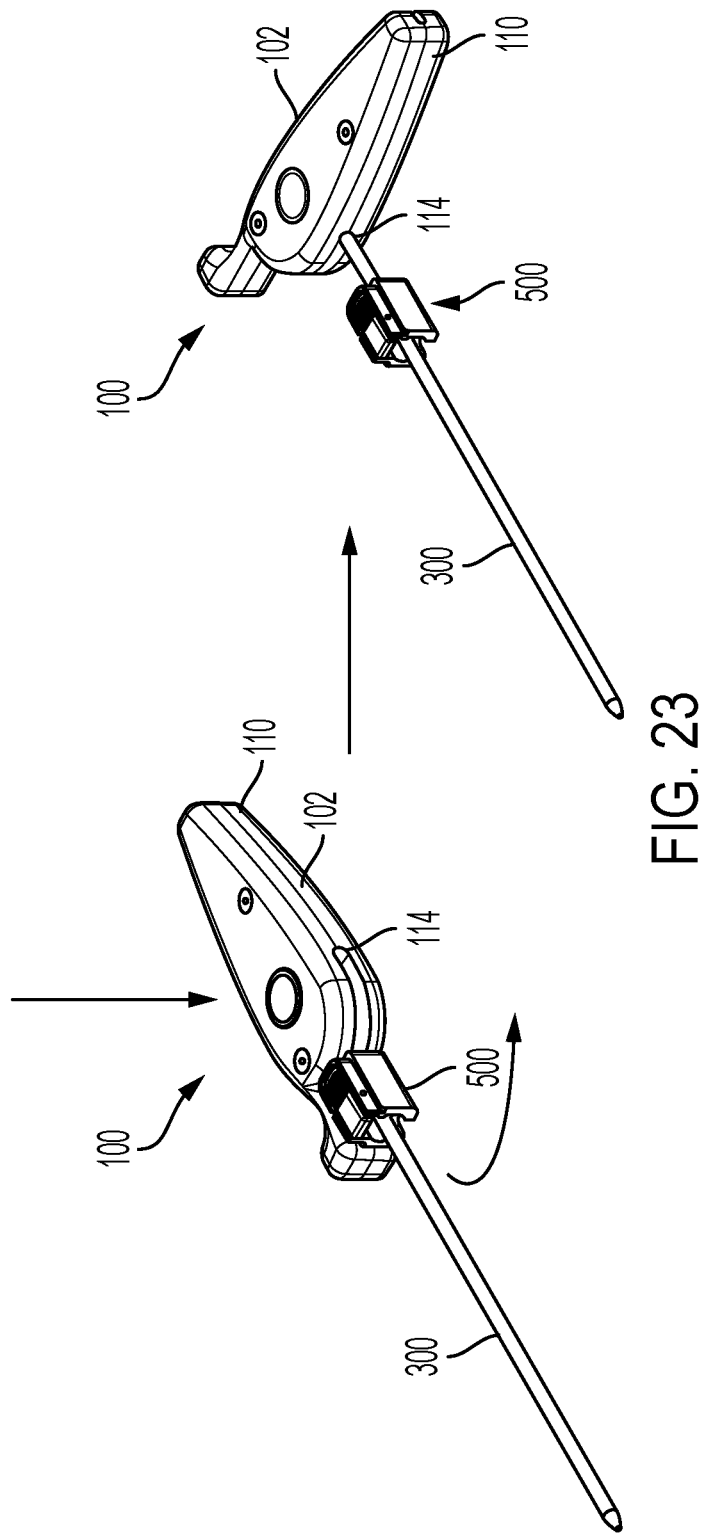
FIG. 23 is a perspective view schematic representation of an obturator assembly rotating between the first configuration and the second configuration, according to an embodiment.

Referring now to FIGS. 22 and 23, there are shown perspective views schematic representations of the obturator assembly 100 in the fully assembled first configuration and the second configuration, respectively, according to embodiments. As shown in FIG. 22, in the first configuration, the obturator shaft 300 extends through the first and second relief areas 134A, 134B (FIG. 19) in the elongated body 102. The obturator shaft 300 is then rotated via the cannulated hub 200 through the first and second relief areas 134A, 134B in the second piece 110 of the elongated body 102 to the channel 114 in order to achieve the second configuration. As shown in FIG. 23, the latch assembly 500 is attached to the obturator shaft 300 such that the latch assembly 500 rotates with the obturator shaft 300 between the first and second configurations. In embodiments depicted in FIGS. 22 and 23, the obturator shaft 300 (and the latch assembly 500) rotates 90 degrees between the first configuration (FIG. 22) and the second configuration (FIG. 23).

Figure 24:
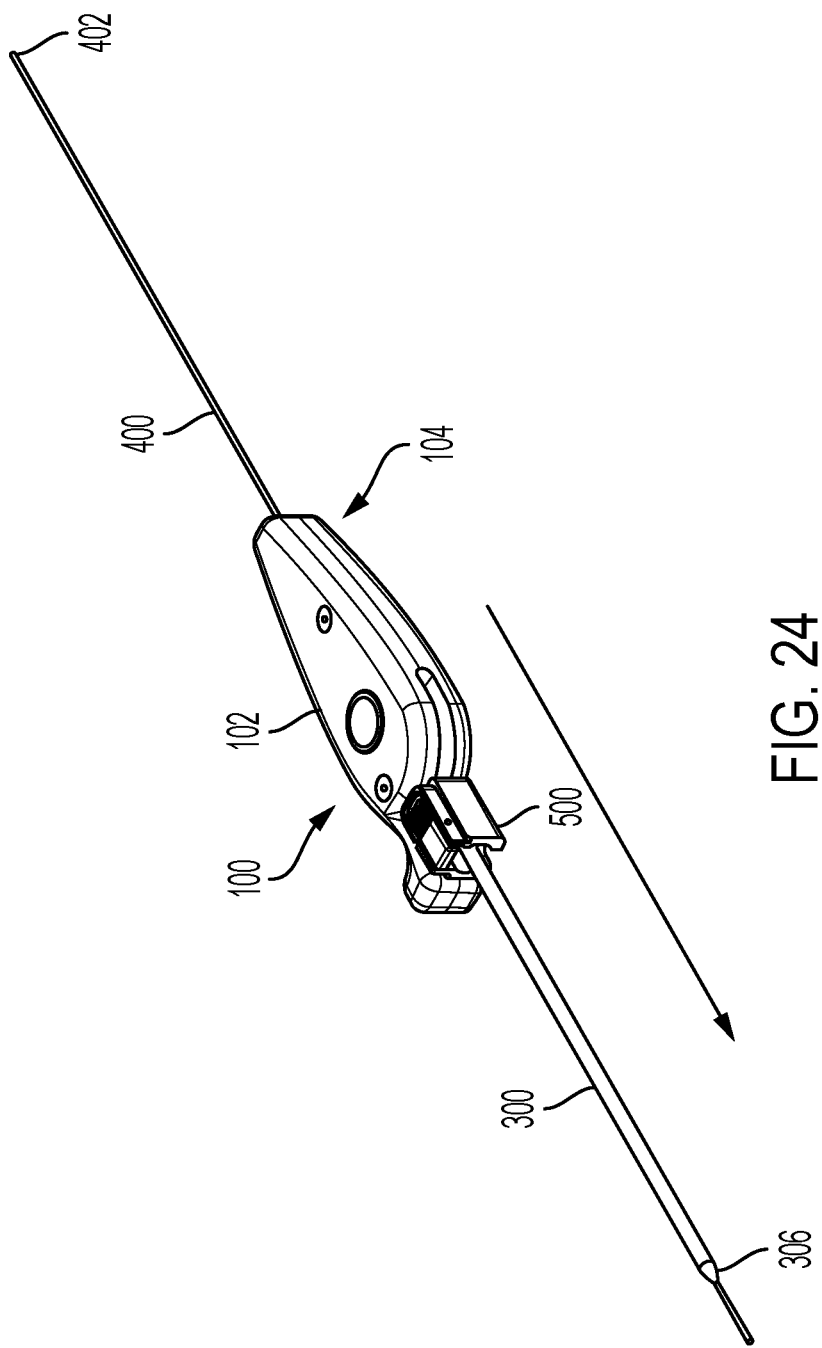
FIG. 24 is a perspective view schematic representation of an obturator assembly in the first configuration with a guide pin extending therethrough, according to an embodiment.
Figure 25:
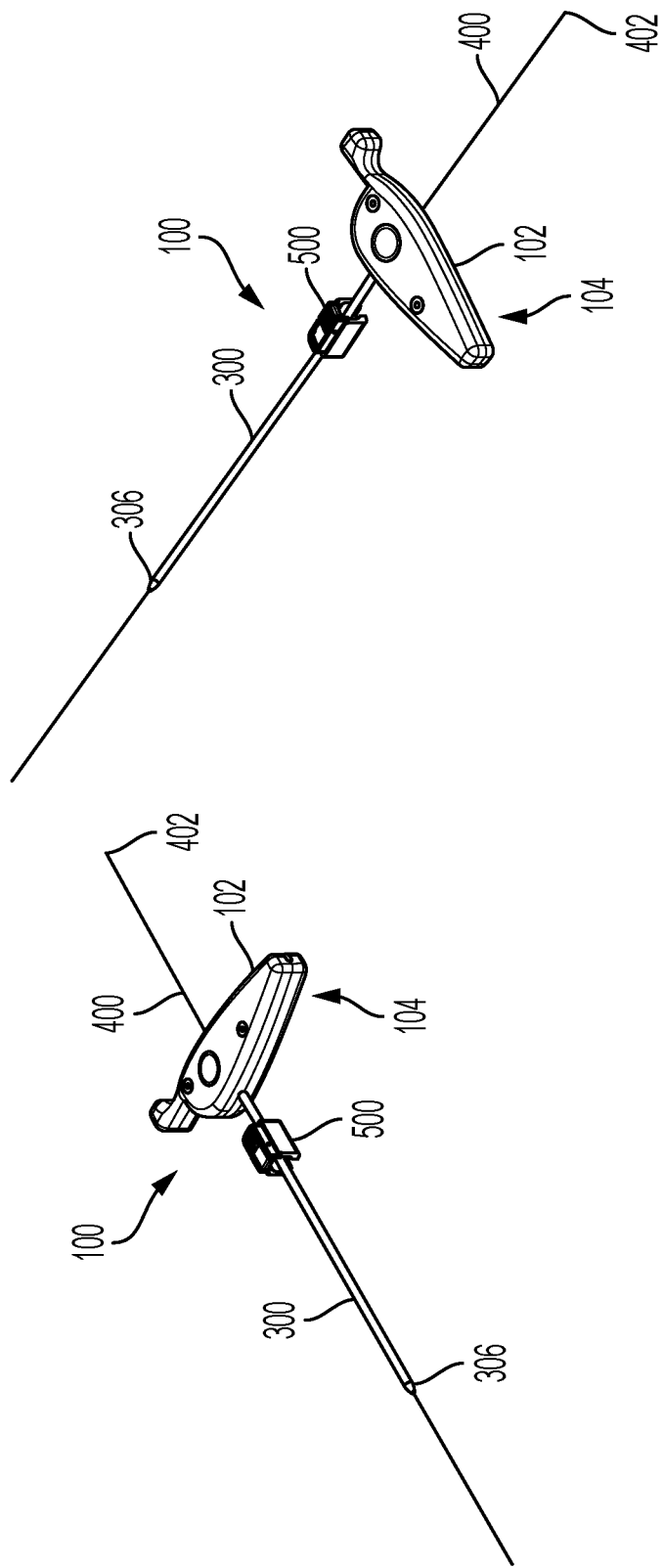
FIG. 25 is a perspective view schematic representation of an obturator assembly in the second configuration with a guide pin extending therethrough, according to an embodiment.

Turning to FIGS. 24 and 25, there are shown perspective views schematic representations of the obturator assembly 100 in the first configuration and the second configuration, respectively, with a guide pin 400 inserted therethrough, according to embodiments. In one embodiment, when using the obturator assembly 100, the guide pin 400 is already in the joint space and the distal, tapered end 306 of the cannulated obturator shaft 300 is placed over the proximal tip 402 of the guide pin 400. The guide pin 400 enters the entire lumen of the obturator assembly 100 and exits out the proximal end 104 of the elongated body 102 as the obturator assembly 100 enters the joint space (the guide pin 400 acts as a guide into the joint space). As shown in FIGS. 24 and 25, the latch assembly 500 rotates with the driver shaft 300 and the guide pin 400 between the first and second configurations.

Referring now to FIG. 27, there is shown a perspective view schematic representation of the obturator assembly 100 in the first configuration with a cannula 600 attached, according to an embodiment. The obturator assembly 100 can be used to place a cannula 600 into the joint space. The purpose of the latch assembly 500 is to attach and remove cannulas 600 from the obturator assembly 100. In the depicted embodiment, the cannula 600 has a diameter that is sized and configured to fit over the obturator shaft 300. The cannula 600 has a proximal end 602 with features 604. The flange 520 (FIG. 19) and channel 522 of the latch 508 grab or otherwise lock onto the features 604 of the cannula 600 when the spring 516 of the latch assembly 500 is in the relaxed state.

Figure 26:
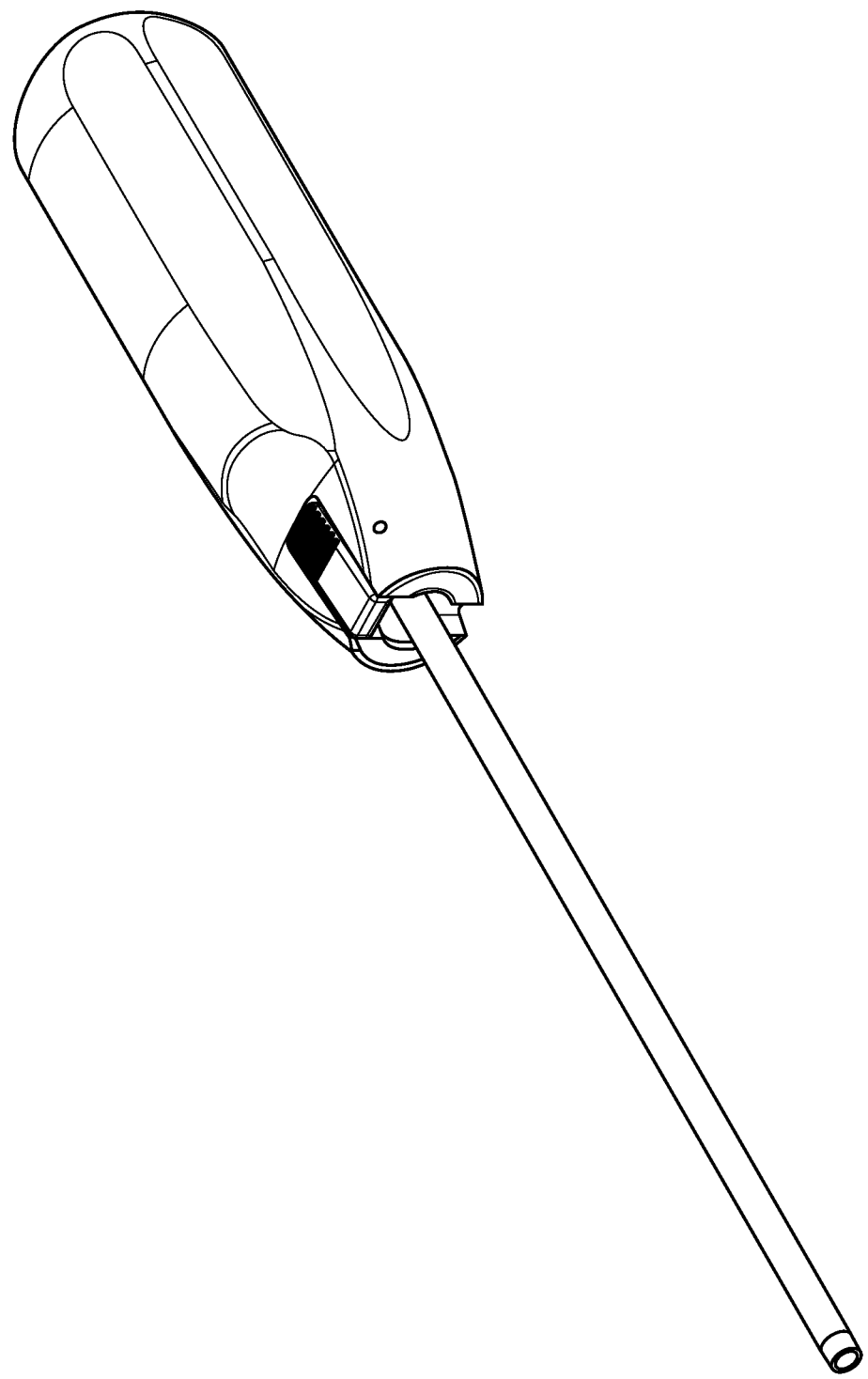
FIG. 26 is a perspective view of an obturator of the prior art.

In the embodiment shown in FIG. 27, the features 604 are threads or ridges on the proximal end 602 of the cannula 600. To lock the cannula 600 over the obturator shaft 300, the proximal end 512 of the latch 508 is pressed. The force on the proximal end 512 rotates the distal end 518 upward, allowing the user to slide the proximal end 602 of the cannula 600 into the open end 504 of the latch sheath 502. Thereafter, the user releases the proximal end 512 of the latch 502, allowing the distal end 518 of the latch 502 to rotate downward onto the features 604 of the cannula 600. The flange 520 and channel 522 at the distal end 518 of the cannula 600 grab onto and lock the cannula 600 in place around the driver shaft 300. Thus, the cannula 600 and the latch assembly 500 rotate with obturator shaft 300, as compared to a traditional, fixed latch assembly, as shown in FIG. 26. Once the cannula 600 is placed into the joint space the obturator assembly 100 is removed by pushing on the proximal end 512 of the latch 508 (FIG. 21). The guide pin 400 can also be removed at this time.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. An obturator assembly, comprising:
an elongated body having a proximal end and a distal end;
a channel extending along an inner surface within the elongated body;
a locking mechanism connected within the elongated body, the locking mechanism rotatable between a first configuration and a second configuration; and
a cannulated obturator shaft removably attached or fixed to the locking mechanism and rotatable between the first configuration and the second configuration via the locking mechanism, wherein the second configuration is orthogonal to the first configuration; and
a latch assembly comprising a latch connected to the cannulated obturator shaft and a latch sheath with an open end and a latch sheath channel extending therethrough, the latch sheath channel configured to receive the cannulated obturator shaft, and wherein the latch assembly is configured to removably couple and lock a cannula around the cannulated obturator and move with the cannulated obturator shaft from the first configuration to the second configuration.

2. The obturator assembly of claim 1, wherein the elongated body has a first piece connected to a second piece.

3. The obturator assembly of claim 2, wherein the inner surface extends along the second piece.

4. The obturator assembly of claim 1, further comprising a first relief area and a second relief area on the inner surface.

5. The obturator assembly of claim 4, further comprising a recess in the inner surface within the elongated body wherein the first relief area and the second relief area converge.

6. The obturator assembly of claim 1, wherein the locking mechanism is a cannulated hub rotatably connected to the elongated body within the recess.

7. The obturator assembly of claim 6, wherein the cannulated hub has an aperture with a driver geometry.

8. The obturator assembly of claim 7, wherein the cannulated obturator shaft has a locking end with a driver geometry configured to mate with the driver geometry of the aperture of the cannulated hub.

9. The obturator assembly of claim 1, wherein the cannulated obturator shaft has a tapered distal end.

10. An obturator assembly, comprising:
an elongated body having a proximal end and a distal end;
a channel extending along an inner surface within the elongated body;
a cannulated hub rotatably connected to the elongated body in a recess, the cannulated hub rotatable between a first configuration and a second configuration;
a locking mechanism integrated with the cannulated hub;
a cannulated obturator shaft removably attached or fixed to the locking mechanism and rotatable between the first configuration and the second configuration via the locking mechanism, wherein the second configuration is orthogonal to the first configuration; and
a latch assembly comprising a latch connected to the cannulated obturator shaft, and a latch sheath with an open end and a latch sheath channel extending therethrough, the latch sheath channel configured to receive the cannulated obturator shaft, and wherein the latch assembly is configured to removably couple and lock a cannula around the cannulated obturator and move with the cannulated obturator shaft from the first configuration to the second configuration.

11. The obturator assembly of claim 10, further comprising a first relief area and a second relief area extending into the inner surface within the elongated body.

12. The obturator assembly of claim 10, wherein the latch is configured to mate with a feature on a cannula.

13. The obturator assembly of claim 10, wherein the latch is spring-biased toward the cannulated obturator shaft.

14. The obturator assembly of claim 10, wherein the latch assembly is rotatable with the cannulated obturator shaft between the first configuration to the second configuration.

15. The obturator assembly of claim 11, further comprising a guide pin extending through a lumen of the cannulated obturator shaft.

16. The obturator assembly of claim 15, wherein between the first and second configurations, the guide pin extends through the first and second relief areas.

17. The obturator assembly of claim 11, wherein between the first and second configurations, the cannulated obturator shaft extends through the first and second relief areas in the elongated body.

18. The obturator assembly of claim 11, further comprising an actuator on an outer surface of the elongated body operably connected to the locking mechanism.

* * * * *